US009914772B2

(12) United States Patent
Honegger et al.

(10) Patent No.: US 9,914,772 B2
(45) Date of Patent: Mar. 13, 2018

(54) ANTIBODIES AGAINST IL-1 BETA

(71) Applicant: Delenex Therapeutics AG, Schlieren (CH)

(72) Inventors: Annemarie Honegger, Zürich (CH); Titus Kretzschmar, Steinhausen (CH); Simone Schmitt, Schlieren (CH); Abdijapar Shamshiev, Zürich (CH); Stefanie Grabulovski, Zürich (CH)

(73) Assignee: Cell Medica Switzerland AG, Schlieren (CH)

( * ) Notice: Subject to any disclaimer, the term of this patent is extended or adjusted under 35 U.S.C. 154(b) by 0 days.

(21) Appl. No.: 14/740,434

(22) Filed: Jun. 16, 2015

(65) Prior Publication Data

US 2016/0194392 A1 Jul. 7, 2016

Related U.S. Application Data

(63) Continuation of application No. PCT/EP2013/076831, filed on Dec. 17, 2013.

(60) Provisional application No. 61/738,223, filed on Dec. 17, 2012.

(30) Foreign Application Priority Data

Feb. 14, 2013 (EP) ..................... 13000746

(51) Int. Cl.
*A61K 39/395* (2006.01)
*C07K 16/24* (2006.01)
*G01N 33/68* (2006.01)

(52) U.S. Cl.
CPC ....... *C07K 16/245* (2013.01); *G01N 33/6869* (2013.01); *C07K 2317/24* (2013.01); *C07K 2317/33* (2013.01); *C07K 2317/35* (2013.01); *C07K 2317/41* (2013.01); *C07K 2317/54* (2013.01); *C07K 2317/55* (2013.01); *C07K 2317/56* (2013.01); *C07K 2317/565* (2013.01); *C07K 2317/569* (2013.01); *C07K 2317/622* (2013.01); *C07K 2317/76* (2013.01); *C07K 2317/94* (2013.01); *G01N 2333/545* (2013.01)

(58) Field of Classification Search
None
See application file for complete search history.

(56) References Cited

U.S. PATENT DOCUMENTS

| 7,531,166 | B2 * | 5/2009 | Masat | ........... | C07K 16/245 424/85.2 |
| 2003/0026806 | A1 | 2/2003 | Witte et al. | | |
| 2010/0239582 | A1 * | 9/2010 | Humphreys | ........... | C07K 16/00 424/136.1 |
| 2011/0159007 | A1 * | 6/2011 | Borras | ........... | C07K 16/241 424/158.1 |

FOREIGN PATENT DOCUMENTS

| WO | 02/16436 | A2 | 2/2002 |
| WO | 03/097697 | A2 | 11/2003 |
| WO | 2004067568 | A2 | 8/2004 |
| WO | 2006081139 | A2 | 8/2006 |
| WO | 2007002261 | A2 | 1/2007 |
| WO | 2009/155725 | A1 | 12/2009 |
| WO | 2009/155726 | A2 | 12/2009 |
| WO | 2009149370 | A1 | 12/2009 |
| WO | 2010028273 | A1 | 3/2010 |
| WO | 2011140522 | A1 | 11/2011 |
| WO | 2012034039 | A2 | 3/2012 |

OTHER PUBLICATIONS

Owyang, A. M., et al. "XOMA 052, a potent, high-affinity monoclonal antibody for the treatment of IL-1 beta-mediated diseases," mAbs, 2011, vol. 3, p. 49-60.
OWyang, A. M., et al., "XOMA 052, an Anti-IL-1 beta Monoclonal Antibody, Improves Glucose Control and beta-Cell Function in the Diet-Induced Obesity Mouse Model", Endocrinology, 151, No. 6, Jun. 1, 2010 (Jun. 1, 2010), pp. 2515-2527.
Holliger, P. and Hudson, P. J., "Engineered antibody fragments and the rise of single domains," Nature Biotechnology, 2005, vol. 23, No. 9, p. 1126-1136.
Cheng, Y.-C. and Prusoff, W. H., "Relationship between the inhibition constant (KI) and the concentration of inhibitor which causes 50 per cent inhibition (I50) of an enzymatic reaction," Biochemical Pharmacology, 1973, vol. 22, p. 3099-3108.
Rammes, G., et al., "Identification of a domain which affects kinetics and antagonistic potency of clozapine at 5-HT3 receptors," PLoS ONE, 2009, vol. 4(8), p. 1-14.
Zhen, J., et al., "Concentration of receptor and ligand revisited in a modified receptor binding protocol for high-affinity radioligands: [3H] spiperone binding to D2 and D3 dopamine receptors," Journal of Neuroscience Methods, 2010, vol. 188(1), p. 32-38.
Dinarello, C.A., "A clinical perspective of IL-1 beta as the gatekeeper of inflammation," Eur. J. Immunol., 2011, vol. 41, p. 1203-1217.
Dinarello, C. A., "Blocking Interleukin-1β in Acute and Chronic Autoinflammatory Diseases," J Intern Med., 269(1): 16-28 (2011).
Dinarello, C. A., "How Interleukin-1β Induces Gouty Arthritis," Arthritis Rheum., 62(11): 3140-3144 (2010).
Honegger, A. and Pluckthun, A., "Yet another numbering scheme for immunoglobulin variable domains: An automatic modeling and analysis tool," Journal of Molecular Biology, 2001, vol. 309, p. 657-670.
Needleman, S. B. and Wunsch, C. D., "A general method applicable to the search for similarities in the amino acid sequence. of two proteins," Journal of Molecular Biology, 1970, vol. 48, p. 443-453.
Contassot, E., et al., "Interleukin-1, inflammasomes, autoinflammation and the skin," Swiss Med Wkly., 142: w13590, pp. 1-10 (2012).
Holliger, P., et al., "Diabodies: small bivalent and bispecific antibody fragments," PNAS USA, 1993, vol. 90: 6444-6448.

(Continued)

*Primary Examiner* — Dong Jiang
(74) *Attorney, Agent, or Firm* — Elmore Patent Law Group, P.C.; Carolyn Elmore; Darlene Vanstone

(57) ABSTRACT

The present invention relates to anti-IL-1 beta antibodies and in particular to monovalent high potency IL-1 beta-binding antibody fragments being highly stable. Such antibodies can be used in the treatment of inflammatory and other diseases as well as in diagnostics. Also provided are related nucleic acids, vectors, cells, and compositions.

34 Claims, 7 Drawing Sheets

(56) References Cited

OTHER PUBLICATIONS

Ewert, S. et al., "Structure-based improvement of the biophysical properties of immunoglobulin VH domains with a generalizable approach," Biochemistry, 2003, vol. 42, p. 1517-1528.

Alfthan, K., et al., "Properties of a single-chain antibody containing different linker peptides," Protein Engineering, 1995, vol. 8, No. 7, p. 725-731.

Niesen, F. H., et al., "The use of differential scanning fluorimetry to detect ligand interactions that promote protein stability," Nature Protocols, 2007, vol. 2(9), p. 2212-2221.

Nicholls, P. J., et al., "Characterization of single-chain antibody (sFv)-toxin fusion proteins produced in vitro in rabbit reticulocyte lysate," Journal of Biological Chemistry, 1993, vol. 268(7), pp. 5302-5308.

Hossler, P., et al., "Optimal and consistent protein glycosylation in mammalian cell culture," Glycobiology, 2009, vol. 19, No. 9, p. 936-949.

Pasut, G. and Veronese, F. M., "State of the art in PEGylation: the great versatility achieved after forty years of research," Journal of Controlled Release, 2012, vol. 161, p. 461-472.

Borras, L., et al., "Generic approach for the generation of stable humanized single-chain Fv fragments from rabbit monoclonal antibodies," Journal of Biological Chemistry, 2010, vol. 285, No. 12, p. 9054-9066.

Alten, R., et al., "The human anti-IL-1β monoclonal antibody ACZ885 is effective in joint inflammation models in mice and in a proof-of-concept study in patients with rheumatoid arthritis", Arthritis Research and Therapy, vol. 10 (R67), (2008).

Bhaskar, V., et al., "Monoclonal antibodies targeting IL-1 beta reduce biomarkers of atherosclerosis in vitro and inhibit atherosclerotic plaque formation in Apolipoprotein E-deficient mice", Atherosclerosis, vol. 216, 2011, pp. 313-320.

Jackson, J. R., et al., "In Vitro Antibody Maturation Improvement of a High Affinity, Neutralizing Antibody Against IL-1beta", The Journal of Immunology, vol. 154, 1995, pp. 3310-3319.

Dinarello, C. A., et al., "Treating inflammation by blocking interleukin-1 in a broad spectrum of diseases", Nature Reviews, vol. 11, 2012, pp. 633-652.

Hou, J., et al., "Design of a superior cytokine antagonist for topical ophthalmic use," PNAS, 110(10): 3913-3918 (2013).

Ruperto, N., et al., "Two Randomized Trials of Canakinumab in Systemic Juvenile Idiopathic Arthritis," N. Engl. J. Med., 367(25): 2396-2406 (2012).

Kahn, P. J., et al., "Higher-dose Anakinra Is Effective in a Case of Medically Refractory Macrophage Activation Syndrome," The Journal of Rheumatology, 40(5): 743-744 (2013).

Launay, D., et al., "Effect of In Vitro and In Vivo Anakinra on Cytokines Production in Schnitzler Syndrome," PLOS ONE, 8(3): e59327 (2013).

Soriano, A., et al., "IL-1β biological treatment of familial Mediterranean fever," Clin Rev Allergy Immunol., 45(1): 117-30 (2013).

Vanderschueren, S., et al., "Canakinumab in Schnitzler syndrome," Semin Arthritis Rheum., 42(4):413-6 (2013).

Vitale, A. et al., "Biological Treatments: New Weapons in the Management of Monogenic Autoinflammatory Disorders," Mediators of Inflammation, vol. 2013, Hindawi Publishing Corporation (2013).

Panka, D. J. et al. "Variable region framework differences result in decreased or increased affinity of variant anti-digoxin antibodies," Proc. Natl. Acad. Sci. USA, 85: 3080-3084 (1988).

Rudikoff, S., et al., "Single amino acid substitution altering antigen-binding specificity," Proc. Natl. Acad. Sci. USA, 79: 1979-1983 (1982).

Lederman, S., et al., "A Single Amino Acid Substitution in a Common African Allele of the CD4 Molecule Ablates Binding of the Monoclonal Antibody, OKT4," Molecular Immunology, 28(11): 1171-1181 (1991).

* cited by examiner

```
DLX2260   1  EIVMTQSPSTLSASVGDRVTITCRASQDISNYLSWYQQKPGKAPKLLIYTSKLHSGVPS   60
DLX2289   1  EIVMTQSPSTLSASVGDRVTITCRASQDISNYLSWYQQKPGKAPKLLIYTSKLHSGVPS   60
DLX2332   1  EIVMTQSPSTLSASVGDRVTITCRASQDISNYLSWYQQKPGKAPKLLIYTSKLHSGVPS   60
DLX2296   1  DIQMTQSPSTLSASVGDRVTITCRASQDISNYLSWYQQKPGKAPKLLIYTSKLHSGVPS   60
DLX2295   1  DIQMTQSPSTLSASVGDRVTITCRASQDISNYLSWYQQKPGKAPKLLIYTSKLHSGVPS   60

DLX2260  61  RFSGSGSGAEFTLTISSLQPDDFATYYCLQGKMLPWTFGQGTKLTVLG            108
DLX2289  61  RFSGSGSGAEFTLTISSLQPDDFATYYCLQGKMLPWTFGQGTKLTVLG            108
DLX2332  61  RFSGSGSGAEFTLTISSLQPEDFATYYCLQGKMLPWTFGQGTKLTVLG            108
DLX2296  61  RFSGSGSGAEFTLTISSLQPEDFATYFCLQGKMLPWTFGQGTKLEIKR            108
DLX2295  61  RFSGSGSGAEFTLTISSLQPEDFATYFCLQGKMLPWTFGQGTKLEIKR            108
```

FIG. 1A

```
DLX2260   1  EVQLVESGGGLVQPGGSLRLSCTASGFSLSTSGMGVGWVRQAPGKGLEWVGHIWWDGDES   60
DLX2289   1  EVQLVESGGGLVQPGGSLRLSCAASGFSLSTSGMGVGWVRQAPGKGLEWVSHIWWDGDES   60
DLX2332   1  EVQLVESGGGSVQPGGSLRLSCAASGFSLSTSGMGVGWVRQAPGKGLEWVGHIWWDGDES   60
DLX2296   1  EVQLVESGGGLVQPGGSLRLSCAFSGFSLSTSGMGVGWVIRQAPGKGLEWVSHIWWDGDES   60
DLX2295   1  EVQLVESGGGSVQPGGSLRLSCAFSGFSLSTSGMGVGWVIRQAPGKGLEWVSHIWWDGDES   60

DLX2260  61  YNPSLKSRFTISRDTSKNTVYLQMNSLRAEDTAVYYCARNRYDPPWFVDWGQGTLVTVSS  120
DLX2289  61  YNPSLKSRFTISRDNSKNTLYLQMNSLRAEDTAVYYCAKNRYDPPWFVDWGQGTLVTVSS  120
DLX2332  61  YNPSLKSRFTISRDTSKNTVYLQMNSLRAEDTASYFCARNRYDPPWFVDWGQGTTVTVSS  120
DLX2296  61  YNPSLKGRFTISKDTSRNTVYLQMNSLRAEDTAVYFCARNRYDPPWFVDWGQGTTVTVSS  120
DLX2295  61  YNPSLKGRFTISKDTSRNTVYLQMNSLRAEDTASYFCARNRYDPPWFVDWGQGTTVTVSS  120
```

FIG. 1B

ANTIBODIES AGAINST IL-1 BETA

RELATED APPLICATIONS

This application is a continuation of International Application No. PCT/EP2013/076831, which designated the United States and was filed on Dec. 17, 2013, published in English, which claims the benefit of U.S. Provisional Application No. 61/738,223, filed on Dec. 17, 2012. This application claims priority under 35 U.S.C. §119 or 365 to EP Application No. 13000746.1, filed Feb. 14, 2013. The entire teachings of the above applications are incorporated herein by reference.

FIELD OF INVENTION

The invention relates to humanized anti-IL-1 beta antibodies, in particular monovalent, highly potent and stable anti-IL-1 beta antibody fragments applicable for therapeutic uses. The invention also relates to nucleic acids encoding such antibodies and antibody fragments, vectors, host containing such sequences, pharmaceutical and diagnostic compositions comprising the antibodies and antibody fragments or nucleic acids, and uses thereof.

BACKGROUND OF THE INVENTION

Interleukin 1 beta (IL-1 beta) is a pro-inflammatory cytokine which is expressed as a precursor called pro-IL-1 beta by activated macrophages, monocytes and dendritic cells. The precursor is cleaved by caspase-1 to form the biologically active and secreted form of IL-1 beta. Binding of IL-1 binds to its receptor, IL-1 receptor type I (IL-1R1), allows the recruitment of a second receptor subunit, the IL-1R accessory protein (IL-1RAP). The formed complex is competent of signal transduction. Being a key mediator in the inflammatory response, the cytokine affects a number of cellular activities such as cell proliferation, differentiation, and apoptosis. Therefore, IL-1 beta is considered an important target for a variety of drugs.

Several antibodies to IL-1 beta have previously been reported. R&D Systems, Inc. produces and sells the murine anti-human IL-1 beta/IL-1F2 antibody MAB201 (R&D Systems, Inc., cat. no. MAB201), a full-length immunoglobulin IgG1, which is produced in hybridoma culture.

MAB201, which displays a half-maximum neutralizing potency range from 6.6 to 20 pM according to the supplier, has been humanized by grafting its CDRs onto human kappa chain germline sequence and gamma chain VH-2 acceptor sequences (US20030026806, AMGEN, Inc.) to yield a full-length immunoglobulin.

XOMA052, also known as AB7 or gevokizumab, is a humanized IgG$_2$, i.e. a full-length immunoglobulin (OWYANG, A., et al. XOMA 052, a potent, high-affinity monoclonal antibody for the treatment of IL-1 beta-mediated diseases. mAbs 2011, vol. 3, p. 49-60; EP 1899378 B, XOMA TECHNOLOGY, Ltd.). Its variable domains were humanized to match a human kappa 1 light chain and a human VH2 heavy chain. Its CDRs are identical to MAB201 with the exception of one conservative point mutation in CDR-H2.

Typically, after CDR-grafting for, e.g., humanization purposes, an antibody having accommodated new CDRs from a CDR-donor antibody experiences a drop in potency when compared to the CDR-donor antibody. It is therefore a true challenge, if successful at all, to further engineer the generated CDR-acceptor antibody such that the potency is close or equal to the CDR-donor antibody.

Moreover, for use in medical treatments it is mandatory, besides providing a good biological potency of the antibody, to generate antibodies with enhanced drug-like properties, e.g., high stability and sufficient solubility.

Hence, there is a need for novel antibodies and in particular antibody fragments, which overcome the disadvantages of the existing antibodies in the art. The invention provides such compounds, as well as methods for preparing and using these.

SUMMARY OF THE INVENTION

In a first aspect, a humanized antibody against IL-1 beta is provided.

In one embodiment, said humanized antibody comprises a variable light chain framework sequence having at least 90% identity to SEQ ID No: 8; and a variable heavy chain framework sequence having at least 90% identity to SEQ ID No: 12.

Additionally or alternatively, said antibody comprises variable light chain CDR-L1, CDR-L2 and CDR-L3 sequences as set forth in SEQ ID Nos: 1, 2, and 3, respectively, or variants thereof, and wherein
position 1 of the light chain is an aspartic acid residue (D);
position 3 of the light chain is a glutamine residue (Q);
position 20 of the light chain is a threonine residue (T);
position 99 of the light chain is a glutamic acid residue (E);
position 105 of the light chain is a phenylalanine residue (F);
position 146 of the light chain is a glutamic residue (E);
position 147 of the light chain is an isoleucine residue (I);
position 148 of the light chain is a lysine residue (K); and/or
position 149 of the light chain is a arginine residue (R), according to AHo numbering.

Additionally or alternatively, said antibody comprises CDR-H1, CDR-H2 and CDR-H3 sequences set forth in SEQ ID Nos: 4, 21, and 6, respectively, or variants thereof, and wherein
position 24 of the heavy chain is an alanine residue (A):
position 25 of the heavy chain is a phenylalanine residue (F);
position 44 of the heavy chain is an isoleucine residue (I);
position 56 of the heavy chain is an serine residue (S);
position 82 of the heavy chain is a lysine residue (K);
position 86 of the heavy chain is an arginine residue (R); and/or
position 105 of the heavy chain is a phenylalanine residue (F), according to AHo numbering.

Preferably, said antibody fragment has a VH domain of human subtype VH3 or VH1b.

The antibodies provided herein are highly stable, i.e., they remain monomeric for prolonged periods of time. This applies in particular to the antibody fragments and more particularly to the scFvs disclosed herein. Stability parameters are crucial factors for providing a viable drug. The more stable a drug, the longer the shelf half-life time. Unstable antibodies tend to dimerize or oligomerize and even precipitate, thereby decreasing shelf-life and finally becoming less suitable for pharmaceutical applications because of, e.g., increased immunogenicity.

For certain therapeutic indications, small antibody fragments have advantages over full-length immunoglobulins because of their smaller size and the lack of the constant region Fc of immunoglobulins. For example, scFv are capable of more efficiently penetrating tissues due to their small size. Further, they display a decreased retention in the systemic circulation as they are unable to bind to Fc receptors such as FcRn eventually leading to higher renal clearance rates. These characteristics of good tissue penetration with subsequent even distribution in the tissue and the rapid elimination of small antibody fragments such as scFv from the systemic circulation are particularly advantageous for both chronic local/topical as well as acute systemic diseases. This practical utility has however been severely limited in the past by low stability and low biological potency of recombinant humanized scFv.

The antibodies provided herein exert very high inhibitory potencies with regard to human IL-1 beta. Monovalent antibody fragments having potency values in the pM-range are particular and not routinely obtained. In addition and typically, an antibody loses affinity to its target upon humanization when compared to the parent non-human antibody. It is therefore a challenge to humanize an antibody such that the affinity parameters are close or equal to the parent antibody. This is particularly true for monovalent antibody fragments which comprise only one variable light and heavy chain, and therefore bind to the target less strongly than bivalent antibodies displaying two light and heavy chains.

A biologically very potent antibody is particularly useful since it allows, e.g., the administration of low amounts of drug to the patient, thereby decreasing the overall costs of treatment. In addition, a more complete neutralization of the molecular target of the disease is rendered feasible.

Moreover, different, novel application routes in animal models as well as in human therapy can be envisioned when applying highest potency antibodies. For example, as to topically applied drugs, although the delivery efficacy may be limited due to the barrier function of the skin stratum corneum and/or other biological structures, the efficacy of treatment is restored by the high potency of the otherwise limited quantity of drug molecules that passes such physiological barriers.

Often, the high amount of a less potent drug which needs to be administered to achieve similar pharmacodynamic effects as with a more potent drug, translates into much higher intravenous or subcutaneous application volumes. Such higher application volumes are a disadvantage for use in animals and humans for two reasons: firstly, the impracticality of treating patients with a high volume of drug, and secondly, antibodies are expensive per unit of mass.

Lower quantities of antibodies required for treatment translate into lower production costs for the drug. In particular antibody fragments are amenable to low production costs since the use of, e.g., bacterial or yeast culture systems is leading to lower costs than with mammalian expression systems typically used for the production of full-length immunoglobulins. The combination of smaller quantities of drug to be administered and cheaper manufacturing processes opens the possibility of more cost-efficient medicines per patient. Thus, a larger number of patients may benefit from such drug.

Stability parameters are other factors crucial for providing a viable medicament. The more stable an antibody drug, the longer the shelf half-life time. The antibodies provided herein are highly stable, i.e., they remain monomeric for prolonged periods of time and also at high concentrations, having the advantage of smaller volumes of administration.

In another aspect, a nucleic acid molecule encoding the antibodies above, a vector comprising said nucleic acid molecule and/or host cells comprising said nucleic acid molecule or said vector are provided.

Also provided is a composition comprising the antibody above, the nucleic acid above, the vector above or the host cell above; and further a suitable carrier, diluent or excipient.

Further provided is a method of treating an IL-1 beta-mediated disease comprising administering to a subject in need thereof said pharmaceutical composition.

The antibodies described herein can, e.g., be used
 (i) as medicament, e.g., in the treatment of an IL-1 beta-mediated disease;
 (ii) in diagnostics;
 (iii) in cosmetics; and/or
 (iv) for detection purposes.

Further provided is a method of producing the antibodies disclosed herein comprising the steps of
 (i) cultivating the host cell above so that the antibody is expressed;
 (ii) recovering the antibody; and
 (iii) optionally purifying the antibody.
Optionally, said method may further comprise at least one step of chemical synthesis.

Further provided is a method of producing the antibodies disclosed herein comprising the steps of
 (a) providing a cell-free system,
 (b) providing a nucleic acid product template,
 (c) allowing for transcription and translation of said nucleic acid product template, thereby expressing the antibody;
 (d) recovering the antibody; and
 (e) optionally purifying the antibody.
Said method may optionally comprise at least one step of chemical synthesis.

Also provided is an in vivo or an in vitro method of detecting the presence of IL-1 beta in a biological sample comprising the steps of
 (i) contacting said biological sample with an antibody disclosed herein under conditions permissive for binding to IL-1 beta, and
 (ii) detecting whether a complex is formed with IL-1 beta.

Further provided is a kit comprising the antibody above together with a packaged combination of reagents with instructions.

BRIEF DESCRIPTION OF DRAWINGS

FIG. 1A depicts alignments of light chain sequences (VL) of anti-IL-1 beta scFv DLX2260, DLX2289, DLX2332, DLX2295 and DLX2296 corresponding to SEQ ID Nos. 17, 16, 20, 19 and 18, respectively. FIG. 1B shows alignments of the corresponding heavy chain sequences (VH). Amino acids differing at the same position are marked bold, CDR sequences are underlined.

DETAILED DESCRIPTION

Figure 2B:
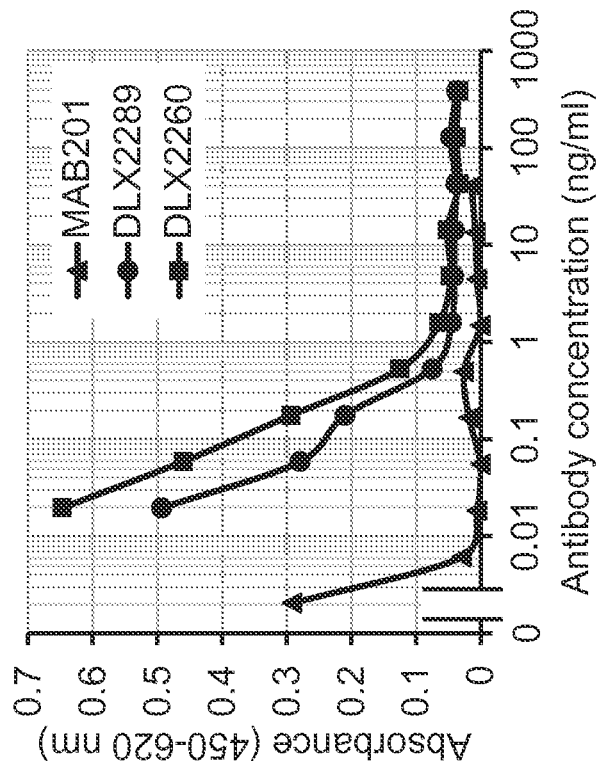
FIG. 2B shows the inhibition of IL-1 beta induced proliferation of D10.G4.1 cells by three different anti-IL-1 beta antibodies. Absorbance differences at a wavelength of 450 nm are plotted as function of the concentration of scFv given in ng/ml. Squares: DLX2260; circles: DLX2289; triangles: MAB201.

So that the invention may be more readily understood, certain terms will be first defined. Unless otherwise defined within the specification, all technical and scientific terms used herein have their art-recognized meaning. Although similar or equivalent methods and materials to those described herein can be used in the practice or testing of the invention, suitable methods and materials are described below. All publications, patent applications, patents, and other references mentioned herein are incorporated by reference in their entirety. In case of conflict the present specification including definitions will prevail. The materials, methods, and examples are illustrative only and not intended to be limiting.

Within the scope of the present invention the term "antibody" refers to full-length immunoglobulins as well as to fragments thereof. Such full-length immunoglobulins may be monoclonal, polyclonal, chimeric, humanized, veneered or human antibodies.

Such antibody can be monovalent or multivalent, i.e. having one or more antigen binding sites. Non-limiting examples of monovalent antibodies include scFv, Fab fragments, dAb, VHH and nanobodies. A multivalent antibody can have two, three, four or more antigen binding sites whereby one or more different antigens can be recognized. Full-length immunoglobulins, F(ab')$_2$ fragments, bis-scFv and diabodies are non-limiting examples of multivalent antibodies; in said exemplary multivalent antibodies, two binding sites are present, i.e. the antibody is bivalent.

In one embodiment the multivalent antibody is bispecific, i.e. the antibody is directed against two different targets or two different target sites on one target molecule. Bispecific antibodies are, e.g., reviewed in MÜLLER, D. and Kontermann, R. E. Bispecific antibodies. Edited by DÜBEL, S. Weinheim: Wiley-VCH, 20 2007. ISBN 3527314539. p. 345-378. In another embodiment the multivalent antibody comprises more than two, e.g., three or four different binding sites for three or four, respectively, different antigens. Such antibody is multivalent and multispecific, in particular tri- or tetra-specific, respectively.

"Antibody fragments" comprise portions of a full-length immunoglobulin essentially retaining the antigen-specificity of said immunoglobulin. Many but not all antibody fragments lack at least partially the constant region (Fc region) of the full-length immunoglobulin. In some embodiments antibody fragments are produced by proteolytic digestion of the full-length immunoglobulin. An antibody fragment may also be a synthetic or recombinant construct comprising parts of the immunoglobulin or immunoglobulin chains (see e.g. HOLLIGER, P. and Hudson, J. Engineered antibody fragments and the rise of single domains. *Nature Biotechnology* 2005, vol. 23, no. 9, p. 1126-1136). Examples of antibody fragments, without being limited to, include scFv, Fab, Fv, Fab', F(ab')$_2$ fragments, dAb, VHH, nanobodies, V(NAR) or minimal recognition units.

"Single chain variable fragments" or "single chain antibodies" or "scFv" are one type of antibody fragments. scFv are fusion proteins comprising the VH and VL of immunoglobulins connected by a linker. They thus lack the constant Fc region present in full-length immunoglobulins, but retain the antigen-specificity of the original immunoglobulin.

The "IC$_{50}$" or "half-maximum inhibitory concentration" is a measure of antagonist drug potency and describes quantitatively the effectiveness of a compound to inhibit a biological or biochemical function. This measure indicates how much of such compound is needed to inhibit by 50% a certain biological or biochemical process. If residual activity is observed, the IC$_{50}$ value is the concentration of the compound at the inflection point of the measured inhibition curve. Although no direct indicator of affinity, both values are correlated via the Cheng-Prusoff equation (CHENG Y. and Prusoff W. H. Relationship between the inhibition constant (Ki) and the concentration of inhibitor which causes 50 percent inhibition (I50) of an enzymatic reaction. *Biochemical Pharmacology* 1973, vol. 22, p. 3099-3108; RAMMES, G., et al. Identification of a domain which affects kinetics and antagonistic potency of clozapine at 5-HT3 receptors. *PLOS one* 2009, vol. 4, p. 1-14; ZHEN, J., et al. Concentration of receptor and ligand revisited in a modified receptor binding protocol for high-affinity radioligands: [$^3$H] spiperone binding to D2 and D3 dopamine receptors. *Journal of Neuroscience Methods* 2010, vol. 188, p. 32-38).

The term "IL-1 beta specific binding" as used herein describes that an antibody binds to IL-1 beta with higher affinity than to a structurally different antigen which does not comprise the IL-1 beta epitope to which such anti-IL-1 beta antibody binds. Specific binding is reflected by a dissociation equilibrium constant (K$_D$) of lower than 1 micromolar. This constant can be determined, e.g., using Quartz Crystal Microbalance (QCM) in an Attana Instrument, or Surface Plasmon Resonance (SPR) technology in a BIACORE instrument.

As used herein, "IL-1 beta" refers to the molecule as described in e.g., Dinarello C. A., A clinical perspective of IL-1 beta as the gatekeeper of inflammation. *Eur. J. Immunol.* 2011, vol. 41, p. 1203-1217. "hIL-1 beta" as used herein refers to human IL-1 beta. "rIL-1 beta" refers to recombinant IL-1 beta. Recombinant IL-1 beta may or may not have an amino terminal methionine residue, depending upon the method by which it is prepared. "rhIL-1" beta refers to recombinant human IL-1 beta. rhIL-1 beta may e.g. be obtained from Peprotech, USA, cat. no. 200-01B. IL-1 beta may also be obtained by isolation from biological samples of human or non-human origin.

"Humanized" antibody refers to a full-length immunoglobulin or a fragment thereof comprising one or more, typically all six CDR regions of a non-human parent antibody or variant thereof, and in which the framework may, e.g., be (i) a human framework, potentially comprising one or more framework residues of the non-human parent antibody, or (ii) a framework from a non-human antibody modified to increase similarity to naturally produced human frameworks. Methods of humanizing antibodies are known in the art, see, e.g., LEGER, O. and Saldanha, J. Antibody Drug Discovery. Edited by WOOD, C. London: Imperial College Press, 2011. ISBN 1848166281, p. 1-23, whereas the functionality is still unpredictable.

"Framework" (FR) refers to the scaffold of the variable antibody domain, either the variable light chain (VL) or variable heavy chain (VH), which embed the respective CDRs. A VL and/or VH framework typically comprises four framework sections, FR1, FR2, FR3 and FR4, flanking the CDR regions. Thus, as known in the art, a VL has the general structure: (FR-L1)-(CDR-L1)-(FR-L2)-(CDR-L2)-(FR-L3)-(CDR-L3)-(FR-L4), whereas a VH has the general structure: (FR-H1)-(CDR-H1)-(FR-H2)-(CDR-H2)-(FR-H3)-(CDR-H3)-(FR-H4).

Figure 7:
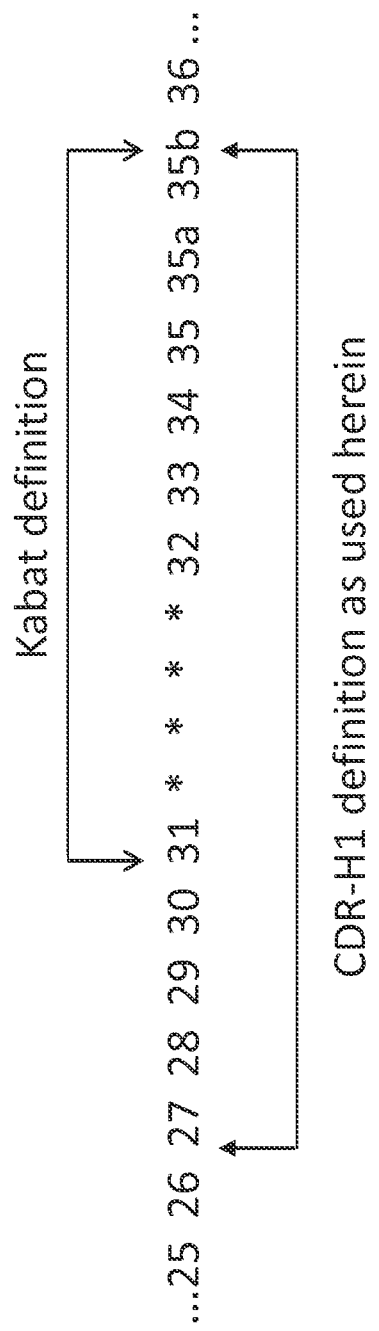
FIG. 7 shows the definition of the CDR-H1 region as used herein and in the Kabat numbering scheme. Arrows indicate the CDR-H1 residues according to the Kabat definition (above) or as used herein (below).

"Complementarity determining region" (CDR) refers to the hypervariable regions of the antibody which mainly contribute to antigen binding. Typically, an antigen binding site comprises six CDRs embedded into a framework. Herein, the CDRs of the VL are referred to as CDR-L1, CDR-L2 and CDR-L3 whereas the CDRs of the VH are referred to as CDR-H1, CDR-H2 and CDR-H3. These can be identified as described in KABAT, E. A., et al. Sequences of Proteins of Immunological Interest. 5th edition. Edited by U.S. DEPARTMENT OF HEALTH AND HUMAN SERVICES. NIH Publications, 1991. p. 91-3242. CDR-H1 as used herein, however, differs from the Kabat definition in that it starts with position 27 and ends prior to position 36 (see FIG. 7 for illustration).

As used herein, the numbering system to identify amino acid residue positions in the VH and VL of the antibody corresponds to the "AHo"-system described by HONEGGER, A. and Plückthun, A. Yet another numbering scheme for immunoglobulin variable domains: An automatic modelling and analysis tool. Journal of Molecular Biology 2001, vol. 309, p. 657-670. The publication further provides conversion tables between the AHo and the Kabat system (KABAT, E. A., et al. Sequences of Proteins of Immunological Interest. 5th edition. Edited by U.S. DEPARTMENT OF HEALTH AND HUMAN SERVICES. NIH Publications, 1991. p. 91-3242).

An "isolated" antibody or nucleic acid is one being identified and separated from at least one component of its natural environment.

The term "identity" as used herein refers to the sequence match between two proteins or nucleic acids. The protein or nucleic acid sequences to be compared are aligned to give maximum identity, for example using bioinformatics tools such as EMBOSS Needle (pair wise alignment; available at www.ebi.ac.uk). When the same position in the sequences to be compared is occupied by the same nucleobase or amino acid residue, then the respective molecules are identical at that very position. Accordingly, the "percent identity" is a function of the number of matching positions divided by the number of positions compared and multiplied by 100%. For instance, if 6 out of 10 sequence positions are identical, then the identity is 60%. The percent identity between two protein sequences can, e.g., be determined using the Needleman and Wunsch algorithm (NEEDLEMAN, S. B. and Wunsch, C. D. A general method applicable to the search for similarities in the amino acid sequence of two proteins. *Journal of Molecular Biology* 1970, vol. 48, p. 443-453) which has been incorporated into EMBOSS Needle, using a BLOSUM62 matrix, a "gap open penalty" of 10, a "gap extend penalty" of 0.5, a false "end gap penalty", an "end gap open penalty" of 10 and an "end gap extend penalty" of 0.5. The % identity or similarity is typically determined over the entire length of the query sequence on which the analysis is performed. Two molecules having the same primary amino acid or nucleic acid sequence are identical irrespective of any chemical and/or biological modification. For example, two antibodies having the same primary amino acid sequence but different glycosylation patterns are identical by this definition. In case of nucleic acids, for example, two molecules having the same sequence but different linkage components such as thiophosphate instead of phosphate are identical by this definition.

"Similar" protein sequences are those which, when aligned, share similar amino acid residues and most often, but not mandatorily, identical amino acid residues at the same positions of the sequences to be compared. Similar amino acid residues are grouped by chemical characteristics of the side chains into families. Said families are described below for "conservative amino acid substitutions". The "percent similarity" between sequences is the number of positions that contain identical or similar residues at the same sequence positions of the sequences to be compared divided by the total number of positions compared and multiplied by 100%. For instance, if 6 out of 10 sequence positions have identical amino acid residues and 2 out of 10 positions contain similar residues, then the sequences have 80% similarity. The similarity between two sequences can, e.g., be determined using EMBOSS Needle.

A "variant" refers to an amino acid or nucleic acid sequence which differs from the parental sequence by virtue of addition (including insertions), deletion and/or substitution of one or more amino acid residues or nucleobases while retaining at least one desired activity of the parent sequence disclosed herein. In the case of antibodies such desired activity may include specific antigen binding. As to a variant nucleic acid sequence, the encoded antibody retains at least one desired activity of the parent antibody as described above. Variants may be naturally occurring, such as allelic or splice variants, or may be artificially constructed.

As used herein, the term "conservative modifications" refers to modifications that are physically, biologically, chemically or functionally similar to the corresponding reference, e.g., similar size, shape, electric charge, chemical properties, including the ability to form covalent or hydrogen bonds, or the like. Such conservative modifications include, but are not limited to, one or more nucleobase and amino acid substitutions.

For example, conservative amino acid substitutions include those in which the amino acid residue is replaced with an amino acid residue having a similar side chain. Amino acid residues being non-essential with regard to binding to an antigen can, e.g., be replaced with another amino acid residue from the same side chain family, e.g., serine may be substituted for threonine. Amino acid residues are usually divided into families based on common, similar side-chain properties, such as:

1. nonpolar side chains (e.g., glycine, alanine, valine, leucine, isoleucine, methionine),
2. uncharged polar side chains (e.g., asparagine, glutamine, serine, threonine, tyrosine, proline, cysteine, tryptophan),
3. basic side chains (e.g., lysine, arginine, histidine, proline),
4. acidic side chains (e.g., aspartic acid, glutamic acid),
5. beta-branched side chains (e.g., threonine, valine, isoleucine), and
6. aromatic side chains (e.g., tyrosine, phenylalanine, tryptophan, histidine).

A conservative substitution may also involve the use of a non-natural amino acid.

"Non-conservative substitutions", i.e. exchanging members of one family against members of another family, may lead to substantial changes, e.g., with respect to the charge, dipole moment, size, hydrophilicity, hydrophobicity or conformation of the antibody, which may lead to a significant drop in the binding activity, in particular if amino acids are affected that are essential for binding to the target molecule. A non-conservative substitution may also involve the use of a non-natural amino acid.

Conservative and non-conservative modifications can be introduced into parental antibodies by a variety of standard techniques known in the art such as combinatorial chemistry, site-directed DNA mutagenesis, PCR-mediated and/or cassette mutagenesis, peptide/protein chemical synthesis, chemical reactions specifically modifying the parental antibody. The variants can be tested by routine methods for their chemical, biological, biophysical and/or biochemical properties.

Nucleic acid hybridization reactions can be performed under conditions of different stringency. "Stringent conditions" are widely known and published in the art. Typically, during the hybridization reaction a SSC-based buffer can be used in which SSC is 0.15 M NaCl and 15 mM citrate buffer having a pH of 7.0. Increasing buffer concentrations and the presence of a denaturing agent increase the stringency of the hybridization step. For example, high stringency hybridization conditions can involve the use of (i) 50% (vol/vol) formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C. with washes at 42° C. in 0.2×SSC and 0.1% SDS; (ii) 50% (vol/vol) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C., or (iii) 10% dextran sulfate, 2×SSC, and 50% formamide at 55° C., followed by a high-stringency wash consisting of 0.1×SSC containing EDTA at 55° C. Additionally or alternatively, one, two or more washing steps using wash solutions of low ionic strength and high temperature can be included in the hybridization protocol using, for example, 0.015 M sodium chloride/0.0015 M sodium citrate/0.1% sodium dodecyl sulfate at 50° C.

Various aspects of the invention are described in further detail in the following subsections. It is understood that the various embodiments, preferences and ranges may be combined at will. Further, depending of the specific embodiment, selected definitions, embodiments or ranges may not apply.

In a first aspect, the invention provides humanized antibodies binding IL-1 beta.

In one embodiment, said humanized antibody comprises a variable light chain sequence having at least 90% sequence identity to SEQ ID No: 8; and a variable heavy chain sequence having at least 90% sequence identity to SEQ ID No: 12.

Also provided is a humanized antibody binding IL-1 beta comprising CDR-H1, CDR-H2 and CDR-H3 sequences set forth in SEQ ID Nos: 4, 21, and 6, respectively, or variants thereof, and wherein
  position 24 of the heavy chain is an alanine residue (A):
  position 25 of the heavy chain is a phenylalanine residue (F);
  position 44 of the heavy chain is an isoleucine residue (I);
  position 56 of the heavy chain is an serine residue (S);
  position 82 of the heavy chain is a lysine residue (K);
  position 86 of the heavy chain is an arginine residue (R); and/or
  position 105 of the heavy chain is a phenylalanine residue (F), according to AHo numbering.

Said antibody may further comprise
  a serine residue (S) at position 12 of the heavy chain,
  a serine residue (S) at position 103 of the heavy chain, and
  a threonine residue (T) at position 144 of the heavy chain, according to AHo numbering.

Additionally or alternatively, the antibody comprises variable light chain CDR-L1, CDR-L2 and CDR-L3 sequences as set forth in SEQ ID Nos: 1, 2; and 3, respectively, or variants thereof, and wherein
  position 1 of the light chain is an aspartic acid residue (D);
  position 3 of the light chain is a glutamine residue (Q);
  position 20 of the light chain is a threonine residue (T);
  position 99 of the light chain is a glutamic acid residue (E);
  position 105 of the light chain is a phenylalanine residue (F);
  position 146 of the light chain is a glutamic residue (E);
  position 147 of the light chain is an isoleucine residue (I);
  position 148 of the light chain is a lysine residue (K); and/or
  position 149 of the light chain is a arginine residue (R), according to AHo numbering.

The antibody disclosed herein may either be a full-length immunoglobulin or an antibody fragment such as, but not limited to, a Fab, a Fab', a F(ab')$_2$, a scFv, a Fv fragment, a nanobody, a VHH or a minimal recognition unit.

In one embodiment, the antibody is monovalent, such as a scFv or a Fab fragment. In another embodiment, the antibody is multivalent. Such multivalent molecule can be bivalent (such as a full-length immunoglobulin or a F(ab')$_2$ fragment) or comprises at least three target binding sites. The multivalent antibody can be a bispecific antibody such as a diabody, a single-chain diabody or a tandem scFv (see, e.g., KONTERMANN, R. E. Methods in Molecular Biology. Edited by LO, B. Totowa, N.J.: Humana Press, 2004. ISBN 1588290921. p. 227-242). Said bispecific antibodies may well use shorter linkers then SEQ ID NO: 14, i.e., having only one to three repeats of the basic motif of SEQ ID NO: 14 (see, e.g., HOLLIGER, P., et al. Diabodies: small bivalent and bispecific antibody fragments. PNAS 1993, vol. 90, no. 14, p. 6444-6448). In another embodiment, the multivalent antibody is a triabody, minibody or tetrabody.

In a preferred embodiment, the antibody and in particular the monovalent antibody fragment above is a scFv. The VH and VL domains can be connected in either orientation, VL-linker-VH or VH-linker-VL, by a flexible linker. In a preferred embodiment, the orientation is VL-linker-VH, i.e. with the light chain variable region at the N-terminal end and the heavy chain variable region at the C-terminal end of the polypeptide.

Such antibody, and in particular the monovalent antibody fragment such as the scFv, is stable. As used herein, the term "stable" refers to the biophysical property of the antibody to remain essentially monomeric in solution after prolonged incubation and/or incubation at elevated temperature.

For example, the antibodies provided herein and in particular the monovalent antibody fragment above, more particularly the scFv, remain monomeric at least to 70%, preferably at least to 75%, and most preferably to 80% after being incubated for 1 month at 37° C. at a concentration of 1 mg/ml in PBS at pH 7.2. Additionally or alternatively, the antibody remains monomeric at least to 80%, preferably at least to 85%, more preferably to 90%, after 1 month at room temperature at a concentration of 1 mg/ml in PBS at pH 7.2.

The percentage of monomers can, e.g., be determined by SEC-HPLC (size exclusion chromatography-high-performance liquid chromatography). A suitable mobile phase for such testing is, e.g., PBS at pH 7.2. The monomer content can be quantified by peak integration of the UV280 nm signal recorded during the protein chromatography. A suitable HPLC system is, e.g., a Dionex Summit HPLC controlled by Chromeleon® 6.5 software that also allows subsequent chromatogram analysis and peak quantification.

In a preferred embodiment, the antibodies provided herein, and in particular the antibody fragment above, comprise a VH domain of human subtype VH3 or VH1b, preferably of subtype VH3. As known in the art, VH domains of other human subtypes, i.e. VH2, VH4 and VH6, usually are unstable in the scFv format which is, e.g., reflected by a lower cooperativity in equilibrium unfolding than VH3 or VH1b (see, e.g. EWERT, S. et al. Structure-based improvement of the biophysical properties of immunoglobulin VH domains with a generalizable approach. *Biochemistry* 2003, vol. 42, p. 1517-1528). Indeed, a library of scFv derived from naturally occurring human full-length immunoglobulins being selected for stability and solubility within yeast cells showed a preference for VH3 (67%) and VH1b (19%), whereas only 9% of VH1a and 5% of VH4 were found; VH2, VH5 and VH6 were not represented at all (WO03/097697, ESBATech AG).

The antibodies disclosed herein are preferably cross-reactive with cynomolgous, rhesus macaque and/or mouse IL-1 beta.

The antibodies provided herein, in particular the antibody fragment above, comprise a variable light chain sequence having at least 90% sequence identity, more preferably at least 94%, 95%, 96%, 97%, 98% or 99% sequence identity to SEQ ID Nos: 7, 8 or 24; and a variable heavy chain sequence having at least 90% sequence identity, more preferably at least 94%, 95%, 96%, 97%, 98% or 99% sequence identity to SEQ ID Nos: 9, 10, 11, 12 or 13.

In one embodiment, the antibodies disclosed herein comprise a variable light chain sequence having at least 90% sequence similarity, more preferably at least 94%, 95%, 96%, 97%, 98% or 99% sequence similarity, to SEQ ID Nos: 7, 8 or 24; and a variable heavy chain sequence having at least 90% sequence similarity, more preferably at least 94%, 95%, 96%, 97%, 98% or 99% sequence similarity, to SEQ ID Nos: 9, 10, 11, 12 or 13.

The antibodies provided herein preferably comprise a VL sequence as set forth in SEQ ID Nos. 7, 8 or 24. Additionally or alternatively, the antibody comprises a VH as set forth in SEQ ID Nos. 9, 10, 11, 12 or 13.

The antibody, in particular in case of a scFv, may comprise a linker sequence. Such linker sequence has typically ten to about 25 amino acids. Usually, such linker peptide is rich in glycines, which confer flexibility, as well as serines and/or threonines for improved solubility. In a preferred embodiment, a (GGGGS)$_4$ linker (SEQ ID NO: 14) or a variant thereof is used. Variations of said motif having three to five repeats may also be used. Further suitable linkers are described, e.g., in ALFTHAN, K. Properties of a single-chain antibody containing different linker peptides. *Protein Engineering* 1995, vol. 8, no. 7, p. 725-731.

In one embodiment, the antibody comprises the sequence as set forth in SEQ ID No.: 16, 17, 18, 19 or 20. In a much preferred embodiment, the antibody comprises the sequence as set forth in SEQ ID No.: 19.

In certain embodiments, variants of the antibodies provided herein are contemplated. For example, it may be desirable to improve antigen binding, antibody-dependent cell-mediated cytotoxicity (ADCC) and/or complement-dependent cytotoxicity (CDC) to increase stability or solubility, to decrease immunogenicity and/or to alter other biological, biochemical or biophysical properties of the antibody. In some embodiments the variant does not show any improvement over the parent antibody.

Variants of the antibodies provided herein may be prepared by protein and/or chemical engineering, introducing appropriate modifications into the nucleic acid sequence encoding the antibody, or by protein/peptide synthesis. Any combination(s) of deletions, substitutions, additions and insertions can be made to the framework or to the CDRs, provided that the generated antibody possesses the desired characteristics for which it can be screened using appropriate methods. Of particular interest are substitutions, preferably conservative substitutions as described above. Preferred conservative substitutions include:

1. Substituting alanine (A) by valine (V);
2. Substituting arginine (R) by lysine (K);
3. Substituting asparagine (N) by glutamine (Q);
4. Substituting aspartic acid (D) by glutamic acid (E);
5. Substituting cysteine (C) by serine (S);
6. Substituting glycine (G) by alanine (A);
7. Substituting histidine (H) by arginine (R) or lysine (K);
8. Substituting isoleucine (I) by leucine (L);
9. Substituting methionine (M) by leucine (L);
10. Substituting phenylalanine (F) by tyrosine (Y);
11. Substituting proline (P) by alanine (A);
12. Substituting serine (S) by threonine (T);
13. Substituting tryptophan (W) by tyrosine (Y);
14. Substituting phenylalanine (F) by tryptophan (W); and/or
15. Substituting valine (V) by leucine (L)

and vice versa.

The antibody described herein may comprise one or more, such as two, three, four, five, six, seven, eight, nine, ten, eleven, twelve or more of such conservative substitutions.

Non-conservative substitutions may lead to more substantial changes, e.g., with respect to the charge, dipole moment, size, hydrophilicity, hydrophobicity or conformation of the polypeptide. In one embodiment, the antibody comprises one or more, such as two, three, four, five, six, seven, eight, nine, ten, eleven, twelve or more of such non-conservative substitutions.

A variant antibody can comprise modifications in the CDRs or in the framework sequences. For example, the CDRs provided herein may comprise one, two, three, four, five or even more modifications. In one embodiment, the CDR-L1, CDR-L2, CDR-L3, CDR-H1, CDR-H2 and CDR-H3 taken as a whole are at least 90%, preferably 91%, 92%, 93%, 94%, 95%, 96%, 97%, 98% or more preferably 99% identical to the CDRs provided herein. Additionally or alternatively, the CDR-L1, CDR-L2, CDR-L3, CDR-H1, CDR-H2 and CDR-H3 taken as a whole are at least 85%, preferably 90%, 91%, 92%, 93%, 94%, 95%, 96%, 97%, 98% or more preferably 99% similar to the CDRs provided herein.

Additionally or alternatively, the VH of the antibody comprises solubility enhancing point mutations. WO2009/155725 (ESBATech, an Alcon Biomedical Research Unit LLC) describes a motif, which has proven to increase the overall solubility of the antibody. The residues are placed at positions located in the interface of the variable domain and the constant domain of an antibody and stabilize antibody fragments, in particular scFv, lacking the constant domain. In particular, at least one, preferably all three of the following residues are present:
  (i) serine (S) at heavy chain amino acid position 12 (according to AHo numbering);
  (ii) serine (S) or threonine (T) at heavy chain amino acid position 103 (according to AHo numbering); and/or
  (iii) serine (S) or threonine (T) at heavy chain amino acid position 144 (according to AHo numbering).

In a preferred embodiment, the antibody has a serine at VH position 12; a serine at VH position 103; and a threonine at VH position 144 (all AHo numbering).

In a preferred embodiment, the antibody disclosed herein comprises a variable light chain of SEQ ID No.: 8 and a variable heavy chain of SEQ ID No.: 12.

Variants may also be prepared by chain shuffling of light and heavy chains. A single light chain can be combined with a library of heavy chains to yield a library of variants. In one embodiment, said single light chain is selected from the group of VL sequences disclosed herein and/or said library of heavy chains comprises one or more of the VH sequences disclosed herein. Likewise, a single heavy chain can be combined with a library of light chains. Preferably, said single heavy chain is selected from the group of VH sequences recited above and/or said library of light chains comprises one or more of the VL sequences recited above.

In one embodiment, a variant VH sequence comprises a sequence selected from the group consisting of SEQ ID Nos.: 9, 10, 11 and 13.

In another embodiment, a variant VL sequence comprises a sequence selected from the group consisting of SEQ ID Nos.: 7 and 24.

Preferably, a variant antibody
  (i) retains specific binding to IL-1 beta, in particular to hIL-1 beta;
  (ii) has a potency ($IC_{50}$) with regard to inhibiting the biological effect of human IL-1 beta of lower than 10 nM, preferably lower than 1 nM, 500 pM, 400 pM, 300 pM, 200 pM, 100 pM, 50 pM, more preferably of lower than 25 pM; and
  (iii) competes with the antibody disclosed herein for binding to IL-1 beta.

The antibodies disclosed herein have high potencies for neutralizing IL-1 beta. Such antibodies have very high inhibitory potencies against human IL-1 beta with an $IC_{50}$ of lower than 10 nM, more preferably lower than about 1 nM, 500 pM, 250 pM, 100 pM, 90 pM, 80 pM, 70 pM, 60 pM, 50 pM, 40 pM, 30 pM, 20 pM, 10 pM and most preferably about 5 pM.

The $IC_{50}$ can, e.g., be determined using a cell based potency assay. In one embodiment, the $IC_{50}$ value above is determined by inhibiting the IL-1 beta induced release of IL-6 from human fibroblasts. Such assay is based on the observation that fibroblasts stimulated with IL-1 beta release IL-6. In the presence of IL-1 beta inhibiting antibodies, the concentration of released IL-6 is reduced. In a preferred embodiment, normal human dermal fibroblasts (NHDF-Neo, e.g., from Lonza Walkersville USA, cat. no. CC-2509) cells are used. Upon incubation with a mixture of hIL-1 beta and the antibody of interest, supernatants are harvested and examined by an IL-6 ELISA such as the R&D Systems Human IL-6 DuoSet ELISA kit (R&D Systems, cat. no. DY206). In one embodiment, the assay is the IL-1 beta neutralization assay as described in example 2. In a preferred embodiment, the assay is the IL-1 beta neutralization assay as described in example 4. The $IC_{50}$ value is the mean value obtained from three independent repetitions of such assay.

In a much preferred embodiment, the antibody has a melting temperature of about 69° C. as determined by differential scanning fluorimetry (DSF), preferably 70° C., 71° C., 72° C., 73° C., 74° C., 75° C., 76° C., 77° C., 78° C., 79° C., and most preferably 80° C. This method is based on the properties of certain dyes being fluorescent only in a hydrophobic environment. For example, protein unfolding can be detected as an increase in fluorescence upon binding of the dye SYPRO® Orange to a heat-denatured protein (NIESEN F. H. et al. The use of differential scanning fluorimetry to detect ligand interactions that promote protein stability. *Nature Protocols* 2007, vol. 2, p. 2212-2221). The stability of a protein can thus be analyzed by thermal denaturation.

In some embodiments, IL-1 beta shows residual activity when contacted with the antibodies disclosed herein in an in vivo and/or an in vitro setting, i.e. the antibody does not completely inhibit the action of IL-1 beta but permits a residual activity signal elicited by IL-1 beta. This may have the advantage of maintaining efficient immune responses. In one embodiment, the antibody allows a residual IL-1 beta activity of about 10%, preferably of about 5% of the assay signal as determined by inhibiting the release of IL-6 from human fibroblasts by 10 pg/ml of IL-1 beta, preferably the assay described in example 2, in the presence of 60 ng/ml of the antibody described herein when compared to antibodies of non-relevant specificity or vehicle control at the same concentration.

Also provided are biosmilars of the antibodies described herein, i.e. compounds showing no meaningful differences in terms of safety, purity and potency of the antibodies above.

Nucleic Acids, Vectors, Host Cells and Method of Production

Each antibody described herein is encoded by a single nucleic acid or by two or more nucleic acids, for example, each encoding at least one variable region. Knowing the sequence of the antibody or of its parts, cDNAs encoding the polypeptide sequence can be generated by methods well known in the art, e.g., by gene synthesis. These cDNAs can be cloned by standard cloning and mutagenesis techniques into a suitable vector such as an expression vector or a cloning vector. Optionally, the variable light chain is encoded by a separate nucleic acid than the variable heavy chain of the antibody. Further, additional sequences such as tags (e.g., a His-tag), constant domains for the production of a Fab or a full-length immunoglobulin, linkers, coding sequences of a second binding specificity or another functional polypeptide such as an enzyme to generate a fusion construct or a bispecific molecule may be included into the genetic construct.

Based on the cloning strategy chosen genetic constructs may generate an antibody having one or more additional residues at the N-terminal or C-terminal end. For example, an N-terminal methionine derived from the start codon or an additional alanine may be present in an expressed polypeptide, unless it has been clipped off post-translationally. It is therefore to be understood that the antibodies disclosed herein comprise the disclosed sequences rather than consist of them.

In one embodiment, the invention provides a nucleic acid sequence comprising at least 300 nucleobases, more preferably at least 350, 400, 450, or 500 nucleobases and having at least 85%, more preferably at least 90%, 91%, 92%, 93%, 94%, 95%, 96%, 97%, 98% or 99% sequence identity to SEQ ID No. 15. In a much preferred embodiment, the nucleic acid sequence is SEQ ID No. 15.

Additionally or alternatively, the invention provides a nucleic acid sequence comprising at least 300 nucleobases, more preferably at least 350, 400, 450, or 500 nucleobases, which hybridizes with the nucleic acid of SEQ ID No. 15 under high stringency conditions.

Basic protocols of standard cloning, mutagenesis and molecular biology techniques are described in, e.g., Molecular Cloning, A Laboratory Manual (GREEN, M. and Sambrook, J. Molecular Cloning: a Laboratory Manual. 4th edition. Cold Spring Harbor Laboratory, 2012. ISBN 1936113422).

Appropriate host cells for the expression of the genetic constructs can be prokaryotic or eukaryotic. Suitable prokaryotic host cells are gram-negative or gram-positive and include species of the *Escherichia, Erwinina, Enterobacter, Klebsiella, Pseudomonas* or *Bacillus* families. Much preferred is *Escherichia coli*, in particular *E. coli* strains BL21 (DE3) (Life Technologies™, cat. no. C6000-03) and Origami™ 2 (DE3) (Novagen, cat. no 71345).

If post-translational modifications such as glycosylation or phosphorylation are desired, eukaryotic host cells are preferable. For example, eukaryotic microbes such as commonly used *Saccharomyces cerevislae* or *Pichia pastoris* strains may serve as host cells. Host cells can also include plant or animal cells, in particular insect or mammalian cells. Suitable mammalian cells include, without being limited to, Chinese Hamster Ovary Cells (CHO), Human Embryonic Kidney Cells (HEK), Human Umbilical Vein Endothelial Cells (HUVEC) or NSO myeloma cells.

The antibody can be produced by expression in a suitable host cell. For example, the expression vectors described above are introduced into a host cell by standard techniques such as electroporation or chemical transformation. The transformed cells are then cultivated under conditions adequate for recombinant protein expression, typically in appropriate nutritional media, optionally modified for inducing promotors, selecting transformants, or amplifying encoding sequences of interest. The antibody protein is recovered from the culture and optionally purified using standard techniques in the art. The yield of recombinant protein may be improved by optimizing media and culture conditions such as pH, temperature or oxygen supply. In prokaryotes the antibody can be produced in the periplasm, intracellularly as inclusion bodies or be secreted into the medium. Upon harvest, the protein can be purified using methods well known in that art such as size exclusion chromatography, ion exchange chromatography, reversed phase chromatography, hydrophobic interaction, mixed mode chromatography and/or affinity chromatography.

In one embodiment, the antibody is produced in a cell-free system. This typically involves in vitro transcription followed by in vitro translation of nucleic acid product templates encoding the proteins described herein, e.g., plasmid DNA or PCR product templates. For example, crude lysates from growing cells are used as basis for cell-free expression systems, providing the necessary enzymes as well as the cellular protein synthesis machinery. The necessary building blocks such as amino acids or nucleobases as well as energy delivering molecules and others can be exogenously supplied. Cell-free expression systems can, for example, be based on lysed rabbit reticulocytes (e.g., Rabbit Reticulocyte Lysate System, Promega, cat. no. L4540), HeLa cells (e.g., 1-Step Human In Vitro Translation Kit, Thermo Scientific, cat. no. 88881), insect cells (e.g., EasyXpress Insect Kit II, Qiagen, cat. no. 32561), wheat germs (e.g., Wheat Germ Extract, Promega, cat. no. L4380), or *E. coli* cells (e.g., PURExpress® In Vitro Protein Synthesis Kit, NEB, cat. no. E6800S). Also, optimized cell-free antibody expression systems for improved disulfide bond generation can be used for production. Commercially available kits include insect cell lysates (e.g., EasyXpress Disulfide Insect Kit, Qiagen, cat. no. 32582) or *E. coli* cell lysates (e.g., EasyXpress Disulfide *E. coli* Kit, Qiagen, cat. no. 32572). Cell-free protein synthesis has, e.g., the advantage of being fast, achieving high product yields, allowing for easy modification of reaction conditions, forming a low degree of or even no by-products. Cell-free protein synthesis may involve biological and/or chemical steps which cannot be conducted in purely biological or chemical production systems. For example, non-natural or chemically-modified amino acids can be incorporated into the protein at desired positions. ScFv-toxin fusion proteins have been successfully produced in cell-free systems (NICHOLLS, P. J., et al. Characterization of single-chain antibody (sFv)-toxin fusion proteins produced in vitro in rabbit reticulocyte lysate. *Journal of Biological Chemistry* 1993, vol. 268, pp. 5302-5308.) Thus, in one embodiment, a method of producing the antibody described herein is provided comprising the steps of
(a) providing a cell-free system,
(b) providing a nucleic acid template encoding the antibody described herein,
(c) allowing for transcription and translation of said nucleic acid product template, whereby the antibody is expressed;
(d) recovering the antibody; and optionally
(e) purifying said antibody.

Additionally or alternatively, a method of producing the antibody described herein comprises at least one step of chemical synthesis. For example, the method may be entirely chemical. In another embodiment, the cell-based or the cell-free production systems described above comprise at least one step of chemical synthesis.

In a preferred embodiment, the antibodies described herein are produced in a cell-based system using an expression vector for intracellular expression in *E. coli*. Upon expression the polypeptide is generated as inclusion bodies within the cells which are subsequently separated from further cell particles followed by solubilisation in a denaturing agent such as guanidine hydrochloride (GndHCl) and refolded by renaturation procedures well known to the skilled person.

Chemical and/or Biological Modifications

In one aspect, the antibody of the instant invention is chemically and/or biologically modified. Such modification may comprise, but is not limited to, glycosylation, PEGylation, HESylation, Albumin fusion technology, PASylation, labelling with dyes and/or radioisotopes, conjugation with enzymes and/or toxins, phosphorylation, hydroxylation and/or sulfation. Likewise, the nucleic acid sequence, the vector and/or the host cell described above can be modified accordingly.

Chemical and/or biological modifications may be conducted, e.g., to optimize pharmacokinetics, pharmacodynamics, water solubility of the protein and/or to lower its side effects. For example, PEGylation, PASylation and/or HESylation may be applied to slow down renal clearance and thereby increase plasma half-life time of the antibody. Additionally or alternatively, a modification may add a different functionality to the protein, e.g., the antibody may be conjugated with a toxin to more efficiently combat cancer cells, or a detection molecule may be added for diagnostic purposes.

Glycosylation refers to a process that attaches carbohydrates to proteins. In biological systems, this process is performed enzymatically within the cell as a form of co-translational and/or post-translational modification. A protein, here the antibody, can also be chemically glycosylated. Typically, but not limited to, glycosylation is (i) N-linked to a nitrogen of asparagine or arginine side-chains; (ii) O-linked to the hydroxy oxygen of serine, threonine, tyrosine, hydroxylysine, or hydroxyproline side-chains; (iii) involves the attachment of xylose, fucose, mannose, and/or N-acetylglucosamine to a phospho-serine; or (iv) in form of C-mannosylation wherein a mannose sugar is added to a tryptophan residue found in a specific recognition sequence. Glycosylation patterns can, e.g., be controlled by choosing appropriate cell lines, culturing media, protein engineering manufacturing modes and/or process strategies (HOSSLER, P. Optimal and consistent protein glycosylation in mammalian cell culture. *Glycobiology* 2009, vol. 19, no. 9, p. 936-949).

Protein engineering to control or alter the glycosylation pattern may involve the deletion and/or the addition of one or more glycosylation sites. The creation of glycosylation sites can conveniently be accomplished by introducing the corresponding enzymatic recognition sequence into the amino acid sequence of the antibody or by adding or substituting one or more of the above enumerated amino acid residues.

It may be desirable to PEGylate the antibody. PEGylation may alter the pharmacodynamic and pharmacokinetic properties of a protein. Polyethylene-glycol (PEG) of an appropriate molecular weight is covalently attached to the protein backbone (see, e.g., PASUT, G. and Veronese, F. State of the art in PEGylation: the great versatility achieved after forty years of research. *Journal of Controlled Release* 2012, vol. 161, no. 2, p. 461-472). PEGylation may additionally reduce the immunogenicity by shielding the PEGylated protein from the immune system and/or alter its pharmacokinetics by, e.g. increasing the in vivo stability of the antibody, protecting it from proteolytic degradation, extending its half-life time and/or by altering its biodistribution.

Similar effects may be achieved by PEG-mimetics, e.g., by HESylating or PASylating the antibody. HESylation utilises hydroxyethyl starch ("HES") derivatives, whereas during PASylation the antibody becomes linked to conformationally disordered polypeptide sequences composed of the amino acids proline, alanine and serine. Said PEG-mimetics and related compounds are, e.g., described in BINDER, U. and Skerra, A. Half-Life Extension of Therapeutic Proteins via Genetic Fusion to Recombinant PEG Mimetics, in Therapeutic Proteins: Strategies to Modulate Their Plasma Half-Lives. Edited by KONTERMANN, R., Weinheim, Germany: Wiley-VCH, 2012. ISBN: 9783527328499. p. 63-81.

The antibody may include a salvage receptor binding epitope. Such salvage receptor binding epitope typically refers to an epitope of the Fc region of an IgG molecule (e.g., IgG1, IgG2, IgG3, or IgG4) and has the effect of increasing the in vivo half-life of the molecule.

Additionally or alternatively, the antibody is labelled with or conjugated to a second moiety which ascribes ancillary functions following target binding. Said second moiety may, e.g., have an additional immunological effector function, be effective in drug targeting or useful for detection. The second moiety can, e.g., be chemically linked or fused genetically to the antibody using known methods in the art.

Molecules which may serve as second moiety include, without being limited to, radionuclides, also called radio-isotopes (e.g., 35S 32P, 14C, 18F, 125I); apoenzymes; enzymes (such as alkaline phosphatase, horseradish peroxidase, beta-galactosidase or angiogenin); co-factors; peptides (e.g., HIS-tags); proteins (incl. lectins, metal-binding domains); carbohydrates (incl. mannose-6-phosphate tag); fluorophores (including fluorescein isothiocyanate (FITC); phycoerythrin; green/blue/red and other fluorescent proteins; allophycocyanin (APC)); chromophores; vitamins (including biotin); chelators; antimetabolites (e.g., methotrexate), liposomes; toxins including cytotoxic drugs such as taxol, gramicidin D or colchicine; or a radiotoxin.

A labelled antibody is particularly useful for in vitro and in vivo detection or diagnostic purposes. For example, an antibody labelled with a suitable radioisotope, enzyme, fluorophore and/or chromophore can be detected by radioimmunoassay (RIA), enzyme-linked immunosorbent assay (ELISA), or flow cytometry-based single cell analysis (e.g., FACS analysis). Similarly, the nucleic acids and/or vectors disclosed herein can be used for detection or diagnostic purposes, e.g., using labelled fragments thereof as probes in hybridization assays. Labelling protocols may, e.g., be found in JOHNSON, I. and Spence, M. T. Z. Molecular Probes Handbook, A Guide to Fluorescent Probes and Labeling Technologies. Life Technologies, 2010. ISBN: 0982927916.

Compositions

The antibody of the instant invention, the nucleic acid sequences or the vector disclosed herein can be provided in a composition which further comprises a suitable carrier, excipient or diluent. Much preferred is a composition comprising an antibody described herein.

Such composition can, e.g., be a diagnostic, a cosmetic or a pharmaceutical composition. For therapeutic or cosmetic purposes, said composition is a pharmaceutical composition comprising an effective amount of antibody described herein and further a pharmaceutical carrier, excipient or diluent, i.e. a carrier, excipient or diluent not being toxic at the dosages and a concentration employed.

Suitable "carrier", "excipients" or "diluents" include, without being limited to: (i) buffers such as phosphate, or organic acids such as citrate; (ii) antioxidants such as ascorbic acid and tocopherol; (iii) preservatives such as 3-pentanol, hexamethonium chloride, benzalkonium chloride, benzyl alcohol, alkyl paraben, catechol, or cyclohexanol; (iv) amino acids, such as e.g. histidine, arginine; (v) peptides, preferably up to 10 residues such as polylysine; (vi) proteins, such as bovine or human serum albumin; (vii) hydrophilic polymers such as polyvinylpyrrolidone; (viii) monosaccharides, disaccharides, polysaccharides and/or other carbohydrates including glucose, mannose, sucrose, mannitol, trehalose, sorbitol, aminodextran or polyamidoamines; (ix) chelating agents, e.g., EDTA or EGTA; (x) salt-forming ions such as sodium or potassium; (xi) metal complexes (e.g., Zn-protein complexes); and/or (xii) ionic and non-ionic surfactants such as TWEEN™, PLURONICS™ or polyethylene glycol (PEG).

Many of said exemplary compounds have different and/or sometimes dual or multiple functions and may, e.g., act as carrier and as diluent. It is also to be understood that the composition may comprise more than one of each carrier, diluent or excipient.

The antibody, the nucleic acid sequences or the vector may be provided on solid support materials such as beads and microparticles. Typically, the molecules are linked to such carrier via a covalent bond (optionally involving a linker), but may also non-covalently adhere to such carrier or admixture. Said beads and microparticles can comprise, for example, starch, cellulose, polyacrylate, polylacetate polyglycolate, poly(lactide-co-glycolide), latex, or dextran.

Therapeutic Applications

The molecules described herein, in particular the antibody, binding member, nucleic acid or vector, are useful as a medicament. Typically, such medicament comprises a therapeutically effective amount of the molecules provided herein. Accordingly, said molecules can be used for the production of a medicament useful in the treatment of IL-1 beta-related disorders.

In one aspect, a method of treating an IL-1 beta-related disorder is provided comprising the steps of administering a pharmaceutically effective amount of the molecules described herein, in particular the antibody, to a subject in need thereof. In one embodiment, the pharmaceutical composition above comprising such pharmaceutically effective amount of the antibody is administered to said subject.

The term "treat" or "treatment" as used herein refers to the administration of a pharmaceutically effective amount of the antibody, nucleic acid, vector or host cell of the instant invention, to a subject in need thereof to prevent, cure, delay the onset and/or progression, reduce the severity of, stabilize, modulate, cure or ameliorate one or more signs and/or symptoms of an IL-1 beta-related disorder. Typically, the antibody, nucleic acid, vector or host cell is provided in a pharmaceutical composition including those previously described herein.

A "therapeutically effective amount" refers to an amount at which the dosage regimen applied yields the desired therapeutic effect, i.e., to reach treatment goals as defined above. The dosage will depend on various factors including patient and clinical factors (e.g., age, weight, gender, clinical history of the patient, severity of the disorder and/or response to the treatment), the nature of the disorder being treated, the particular composition to be administered, the route of administration, and other factors.

The subject in need of such treatment can be a human or a non-human animal, e.g., a mouse, rat, rabbit, monkey, dog, horse, cow, chicken, guinea pig or pig. Typically, the subject is diagnosed with an IL-1 beta-related disorder or may acquire such a disorder.

Examples of IL-1 beta-related disorders, in which antagonist of IL-1 beta have shown therapeutic effects include, without being limited to, proliferative diabetic retinopathy, gouty arthritis, Schnitzler syndrome, systemic juvenile idiopathic arthritis, rheumatoid arthritis, acute gouty arthritis, chronic gouty arthritis, urticaria, vasculitis, type 1 diabetes, type 2 diabetes, ankylosing spondylitis, recurrent multifocal osteomyelitis, relapsing polychondritis, cyropyrin-associated periodic syndrome (CAPS), Behçet's disease, familial mediterranean fever, chronic obstructive pulmonary disease, polymyalgia rheumatic, NALP3-mutations, pyoderma gangrenosum, chronic idiopathic urticarial, osteoarthritis, wet age-related macular degeneration, dry eye syndrome, pustular psoriasis, synovitis-acne-pustulosis-hyperostosis-osteitis syndrome, macrophage activation syndrome, periodic fever-adenitis-pharyngitis-aphthous ulcer syndrome, adult-onset Still's disease, mevalonate kinase deficiency, atherosclerosis, TNF-receptor associated periodic syndrome (TRAPS), acne vulgaris and/or acne inversa.

The term "CAPS" or cryopyrin-associated periodic syndrome is to be understood to include each of familial cold autoinflammatory syndrome (FCAS), Muckle-Wells syndrome (MWS) and neonatal-onset multisystem inflammatory disease, also known as chronic infantile neurological, cutaneous and articular (CINCA) syndrome.

The pharmaceutical composition may be applied by different administration routes. Administration can be conducted, for example, but not limited to, parenterally, e.g., intramuscularly, subcutaneously, epicutaneously, intravenously as a bolus or by continuous infusion, intraarticularly, intrasynovially, intracerebrally, intracerebrospinally, intrathecally, epidurally, or intraperitoneally; orally; rectally; urogenitally; topically, e.g., to the skin or the eye; intravitreally; intraocularly; oticly; intranasally; by inhalation; dermally such as intradermally or transdermally; sublingually; buccally, for example. Preferred are the topical, rectal, intranasal, intravenous and/or intradermal routes of administration.

The antibody of the instant invention, the nucleic acid sequences, the vector or host cell can be combined with one or more further therapeutically effective compound. Said compound may either be capable of disrupting signalling via the IL-1 receptor, or alternatively inhibit one or more different targets such as, e.g., other mediators of inflammatory responses. Such compound(s) can be administered simultaneously or sequentially.

For therapeutic applications, the antibody may also be radiolabelled or linked to a toxin or linked to another effector function as described above.

Diagnostic Applications and/or Detection Purposes

The antibody of the instant invention may be used for detection or diagnostic purposes in vivo and/or in vitro. For example, a wide range of immunoassays involving antibodies for detecting the expression in specific cells or tissues are known to the skilled person. Likewise, the nucleic acid sequence, the vector and/or the host cell described previously can be used accordingly as detailed in this section. In one embodiment, the method is not practised on the human or animal body.

For such applications the antibody, the nucleic acid sequence, the vector or the host cell disclosed herein may be either labelled or unlabelled. E.g., an unlabelled antibody may be used and detected by a secondary antibody recognizing an epitope on the antibody described herein.

In another embodiment, the antibody, nucleic acid sequence, vector and/or host cell is conjugated with one or more substances which can be recognized by a detector substance(s), e.g., the antibody being conjugated with biotin which can be detected by streptavidin. Likewise, the nucleic acids and/or vectors disclosed herein can be used for detection or diagnostic purposes, e.g., by using labelled fragments thereof as probes in hybridization assays.

In certain embodiments, any of the molecules provided herein, in particular the antibody, is useful for detecting the presence of IL-1 beta, preferably including full-length IL-1 beta, fragments thereof and/or precursors thereof, in a sample, preferably biological sample. The term "detecting" encompasses quantitative and/or qualitative detection. In certain embodiments, a biological sample comprises a cell or tissue from human patients. Non limiting examples of biological samples include blood, urine, cerebrospinal fluid, biopsy, lymph and/or non-blood tissues.

In certain embodiments, the method comprises contacting the biological sample with an anti-IL-1 beta-antibody as described herein under conditions permissive for binding of the antibody to IL-1 beta and detecting whether a complex is formed between the antibody and IL-1 beta. Such method may be an in vitro or in vivo method. In one embodiment, an anti-IL-1 beta antibody is used to select subjects eligible for therapy with the antibody described herein, e.g., where IL-1 beta is a biomarker for selection of patients.

In another aspect, the antibody is used in cosmetic applications, e.g., for improving the aesthetic appearance of skin.

In a further aspect, a kit is provided comprising the antibody, a packaged combination of reagents with instructions for performing the detection or diagnostic assay. The reagents are typically provided in predetermined amounts of dry powders, usually lyophilized, including excipients which after dissolution will provide a reagent solution having the appropriate concentration. Other additives such as stabilizers and/or buffers may also be included. If the antibody is labelled with an enzyme, the kit will typically include the according substrates and cofactors. Likewise, any binding member, the nucleic acid sequence, the vector and/or the host cell described previously can be used accordingly as detailed in this section.

EXAMPLES

Example 1—Design of Anti-Human IL-1 Beta Antibodies

Variable heavy and light chains of AB7 were linked by the peptide linker of SEQ ID No.: 14 to yield a scFv which turned out to be unstable.

CDRs of the anti-human IL-1 beta antibody comprising SEQ ID No.: 22 and SEQ ID No.: 23 were identified and grafted onto two stable human scFv frameworks, each consisting of an N-terminal human light chain variable region, a linker sequence and a C-terminal human heavy chain variable region. Both scFv frameworks differ from each other in five amino acid positions in the heavy chain. The resulting two scFvs were termed DLX2260 and DLX2289 (see FIG. 1).

The DLX2289 framework is derived from a human immunoglobulin described in WO 03/097697 A (ESBATech AG), whereas the DLX2260 framework is derived thereof; the VH framework sequence of the latter has been modified for humanization and stabilization of rabbit antibodies, see, e.g., WO 2009/155726 A (ESBATech, AN ALCON BIO-MEDICAL RESEARCH UNIT LLC; BORRAS, L., et al. Generic approach for the generation of stable humanized single-chain Fv fragments from rabbit monoclonal antibodies. Journal of Biological Chemistry 2010, vol. 285, no. 12, p. 9054-9066).

The scFvs were expressed as inclusion bodies in E. coli (BL21 (DE3); Novagen, cat. no. 69450-3). After harvesting the cells the inclusion bodies were isolated and purified. The proteins were refolded by standard methods and monomeric scFvs were purified using size exclusion chromatography. Monomeric peak fractions were collected and characterized for antigen binding and IL-1 beta neutralization potency in a cell-based assay.

Example 2—IL-1 Beta Binding and Neutralization by DLX2260 and DLX2289

Figure 2A:
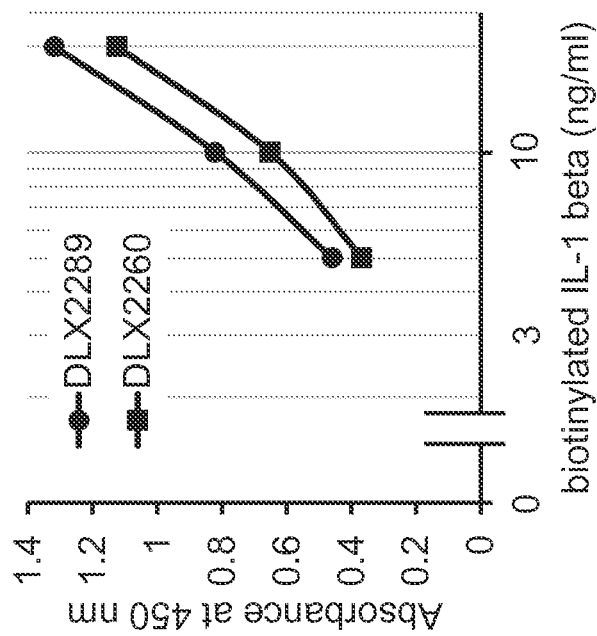
FIG. 2A shows the results of an ELISA to determine the binding of DLX2260 and DLX2289 to biotinylated rhIL-1 beta at various concentrations. Absorbance differences at a wavelength of 450 nm are plotted as function of the concentration of biotinylated IL-1 beta given in ng/ml. Squares: DLX2260; circles: DLX2289.

In an ELISA, the recognition of recombinant human (rh) IL-1 beta by DLX2260 and DLX2289 was confirmed. The scFvs were coated on Maxisorp 96-well microplates at a concentration of 10 mcg/ml overnight at 4° C. in 50 mM Glycine, 50 mM NaCl, pH 10.0. After blocking with 5% non-fat dry milk, biotinylated rhIL-1 beta (R&D systems, cat. no. NFLB0) was added at concentrations ranging from 5 to 20 ng/ml. Bound IL-1 beta was detected by Streptavidin-HRP (BD Pharmingen, cat. no. 554060). The ELISA was developed with BM Blue POD substrate (Roche Applied Science) and the absorbance was measured at 450 nm. The results (see FIG. 2A) show that both scFvs bind equally well to rhIL-1 beta.

The potency of DLX2260 and DLX2289 to neutralize the biological function of human IL-1 beta was analysed in a cell proliferation assay using D10.G4.1 mouse T helper cells (DSMZ, cat. no. ACC45). D10.G4.1 cells were seeded in 96-well tissue culture plates at 4,000 cells per well in RPMI 1640 w/o phenolred (Gibco, Life Technologies, cat. no. 32404014) supplemented with 10% FBS (Gibco, Life Technologies, cat. no. 10270106), 2 mM glutamine (Gibco, Life Technologies, cat. no. 25030024), 1% PenStrep (Gibco, Life Technologies, cat. no. 15070063) and 10 ng/ml of rhIL-2 (Peprotech, cat. no. 200-02), and cultured for 4-6 hours. The scFvs and control antibody (R&D systems, cat. no. MAB201) were pre-incubated with rhIL-1 beta (Peprotech, cat. no. 200-01B) in cell culture media for 2 hours at 37° C. The mixtures were added to the cells at a final concentration of 10 pg/ml of rhIL-1 beta. The positive proliferation control contained 10 pg/ml of rhIL-1 beta only. The cells were cultured for an additional 48 hours. IL-1 beta-induced proliferation was quantified by addition of XTT (Sigma-Aldrich, cat. no. X4251-100MG) at a concentration of 1 mg/ml in RPMI w/o phenolred with 25 mcM phenazine methosulfate (Sigma-Aldrich, P9625-1G). The cells were incubated with XTT solution for 4 hours at 37° C. Absorbance was determined at 450 nm and at the reference wavelength of 620 nm. Both DLX2260 and DLX2289 inhibited IL-1 beta-induced cell proliferation (see FIG. 2B) with similar efficiency. Compared to the control full-length immunoglobulin MAB201 (R&D systems, cat. no. MAB201), cell proliferation is not inhibited completely, approximately 5% of cells continued growing even at highest concentrations of scFvs.

Example 3—Engineering of DLX2260

DLX2260 was chosen as starting point for framework mutations to improve its capability of human IL-1 beta neutralization. Several mutations were introduced in the light chain as well as the heavy chain frameworks. One position in CDR-H2 was also mutated. Additionally, three amino acid positions in the heavy chain framework that were known to improve solubility of scFvs (see WO2009/155725, ESBATech, an Alcon Biomedical Research Unit LLC) were substituted by amino acids with more hydrophilic side chains. In total, three different scFvs were designed (see FIG. 1). DLX2332 is 97% identical to DLX2260, whereas DLX2296 is 93% identical to DLX2260. DLX2295 contains the same mutations as DLX2296 but includes in addition the three solubility substitutions as described above. DLX2295 is 92% identical to DLX2260.

DNA sequences encoding the three scFvs were cloned into a bacterial expression vector, proteins were expressed and purified as described above. Monomeric scFvs were characterized for their IL-1 beta binding, neutralization and stability characteristics.

Example 4—IL-1 Beta Binding and Neutralization by DLX2295, DLX2296 and DLX2332

Figure 3B:
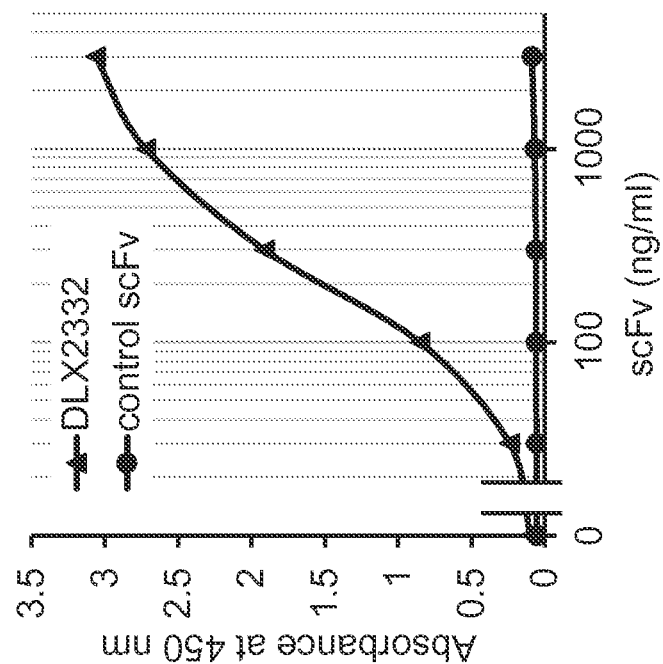
FIG. 3A shows the binding of DLX2295 and DLX2296 to rhIL-1 beta in an ELISA. Absorbance differences at a wavelength of 450 nm are plotted as a function of the concentration of scFv given in ng/ml. Squares: control scFv; circles: DLX2296; triangles: DLX2295. The result for the same experiment performed with DLX2332 is given in FIG. 3B. Absorbance differences at a wavelength of 450 nm are plotted as a function of the concentration of scFv given in ng/ml. Circles: control scFv; triangles: DLX2332.
Figure 3A:
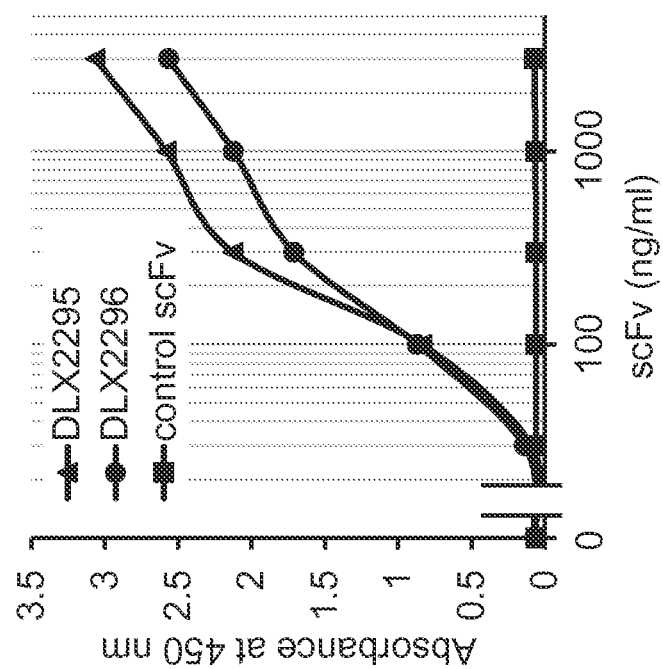

The recognition of rhIL-1 beta by DLX2295, DLX2296 and DLX2332 was confirmed by ELISA (FIGS. 3A and 3B).

A scFv of irrelevant specificity was used as a control. rhIL-1 beta (Peprotech, cat. no. 200-01B) was coated to NUNC 96-well Maxisorp immunoplates. After blocking scFvs were titrated from 10 to 3,000 ng/ml. Bound scFvs were detected by Protein L-HRP (Sigma-Aldrich, cat. no. P3226), and the ELISA was developed using BM Blue POD substrate (Roche Applied Science, cat. no. 11484281001). For quantification purposes, the absorption was measured at 450 nm using VersaMax microplate reader (Molecular Devices).

A fibroblast assay was performed to determine the potency of a compound to neutralize IL-1 beta activity. Human dermal fibroblasts (NHDF-Neo, cat. no. CC-2509, Lonza Walkersville, USA), upon activation by IL-1 beta, specifically release IL-6 which is quantifiable by ELISA. Neutralization of IL-1 beta decreases the amount of IL-6 released from such fibroblasts. The inhibitory potency of anti-IL-1 beta antibodies is usually quantified by measuring the half-maximal reduction ($IC_{50}$) of IL-1 beta-induced IL-6 release. Human dermal fibroblasts were seeded in 96-well microplates at 5,000 cells/well about 16-20 hours prior to addition of samples containing the stimulus IL-1 beta. The fibroblasts were cultured in fibroblast basal medium (FBM; Lonza, cat. no. CC-3131) with supplements (hFGF-B, insulin, FBS, GA-1000) as described by the cell supplier (Lonza Walkersville, USA: Clonetics™ Dermal Fibroblast Cell Systems).

Before seeding, FBM was removed and cells were washed with Dulbecco's Modified Eagle Medium (DMEM; Gibco, Life Technologies, cat. no. 11880) to remove growth factors. The cells were then cultured for 7 hours in DMEM media supplemented with 2% FBS. Antibodies were pre-incubated in DMEM media supplemented with 2% FBS with rhIL-1 beta for 1 hour at 37° C. The mixture was added to the cells at a final concentration of 10 pg/ml of IL-1 beta. As a control, 10 pg/ml of rhIL-1 beta was added to cells without any anti-IL-1 beta antibody. The cells were incubated with the IL-1 beta/anti-IL-1 beta antibody mixture for 18-24 hours, and cell culture supernatants were analyzed for IL-6 release using the Human IL-6 DuoSet ELISA Kit according to the manufacturer's instructions (R&D Systems, USA, cat. no. DY206).

Figure 4:
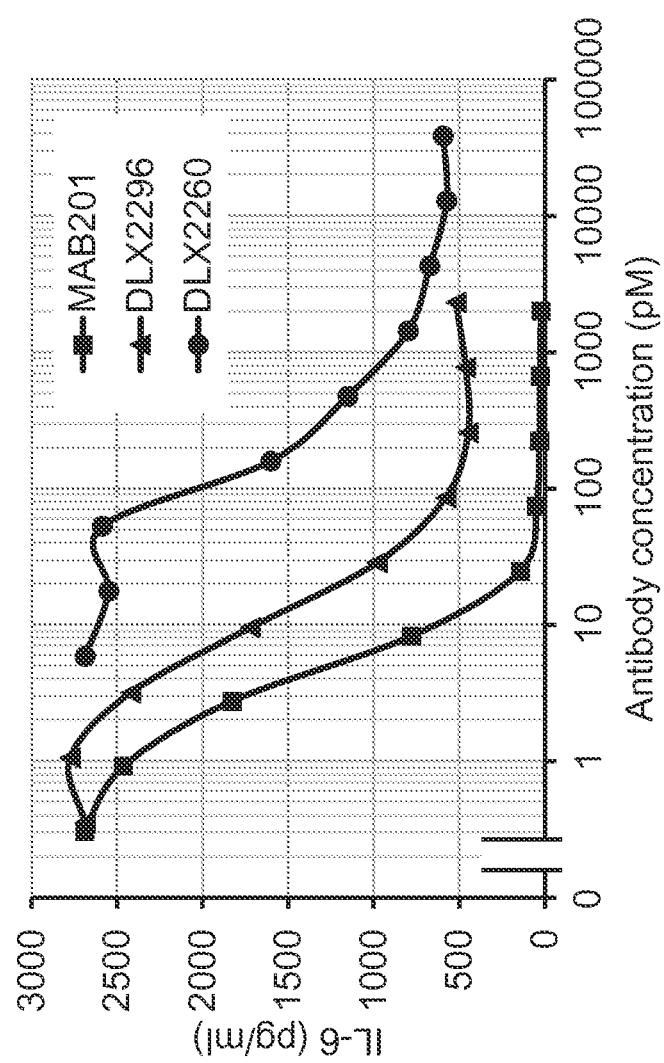
FIG. 4 shows the inhibition of rhIL-1 beta biological activity in a human fibroblast assay. The potency of scFvs DLX2260 and DLX2296 as well as of the control antibody MAB201 is compared. The y-axis indicates the amount of released IL-6 from human fibroblasts in pg/ml; the x-axis indicates the concentration of applied antibodies in pM. Squares: MAB201; circles: DLX2260; triangles: DLX2296.
Figure 5:
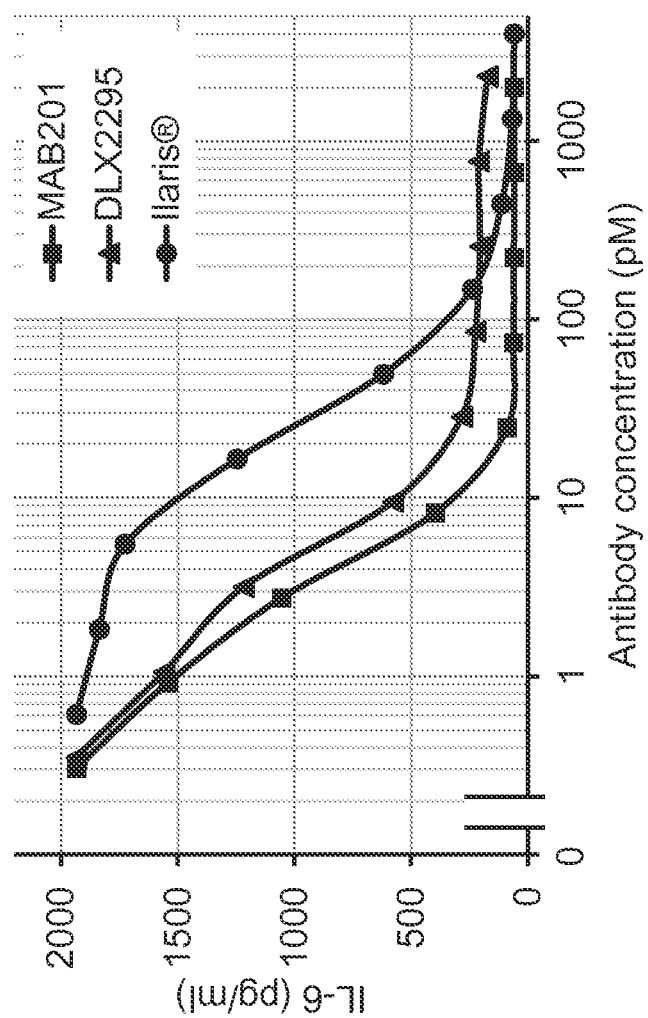
FIG. 5 shows the inhibition of rhIL-1 beta biological activity by DLX2295 in a human fibroblast assay. In the same experiment, the positive control antibodies MAB201 and Ilaris® were analyzed. The y-axis indicates the amount of released IL-6 from human fibroblasts in pg/ml; the x-axis indicates the concentration of applied antibodies in pM. Squares: MAB201; triangles: DLX2295; circles: Ilaris®.
Figure 6:
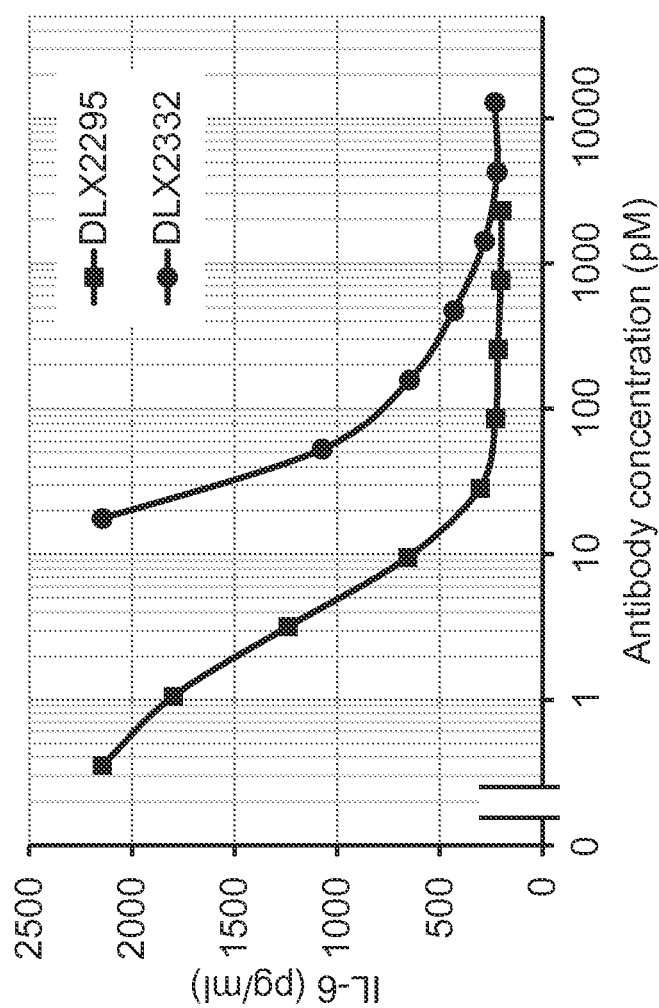
FIG. 6 shows the IL-1 beta neutralization capacity of DLX2332 in comparison to DLX2295 in a human fibroblast assay. The y-axis indicates the amount of released IL-6 from human fibroblasts in pg/ml; the x-axis indicates the concentration of applied antibodies in pM. Squares: DLX2295; circles: DLX2332.

DLX2260, DLX2295, DLX2296 and DLX2332 were assessed for their IL-1 beta neutralization capacity in the human dermal fibroblast assay (NHDF-Neo, cat. no. CC-2509, Lonza Walkersville, USA) as described above. As further controls, anti-IL-1 beta full-length immunoglobulins such as MAB201 (R&D systems, USA, cat. no. MAB201) and Canakinumab (Novartis, Ilaris®) were used. In one experiment, MAB201, DLX2296 and DLX2260 were compared (FIG. 4). In another experimental series, MAB201, DLX2295 and Canakinumab were assayed in parallel (FIG. 5). Finally, the neutralizing efficacy of DLX2295 and DLX2332 were compared (see FIG. 6). MAB201 and DLX2295 displayed the lowest $IC_{50}$ both with approximately 2-5 pM, whereas DLX2296 showed an $IC_{50}$ (considering 20% residual activity) of about 8 pM and 2260 an $IC_{50}$ (considering 20% residual activity) of about 100 pM. The $IC_{50}$ values are mean values of three independent experiments. The monovalent scFv DLX2295 is thus as potent as the bivalent MAB201 IgG. For all scFvs (DLX2295, DLX2296, DLX2260 and DLX2332) tested in the fibroblast assay residual activity was observed, i.e., the IL-1 beta activity was not inhibited completely. This observation is consistent with the results obtained in the D10.G4.1 proliferation assay.

Example 5—Stability

DLX2295 protein stability at different temperatures was assessed. To this end, HPLC (Dionex, Summit system) size exclusion chromatography (Tosoh, TSKgel G2000SWxl, cat. no. 08540) was deployed to determine the percentage of monomeric, non-degraded scFv protein after one month at RT in PBS pH 7.2. The percentage of monomer was measured at the starting point of the study (T0) and after one month for 0.6 mg/ml of DLX2295. The results of the stability study are listed in table 1.

TABLE 1

|  | monomer content |
| --- | --- |
| DLX2295, T0 | 98% |
| DLX2295, stored at RT for 1 month | 93% |

The thermal stability of DLX2260, DLX2289, DLX2295, DLX2296 and DLX2332 was analysed by differential scanning fluorimetry (DSF). For this measurement a real-time PCR device (Corbett, Rotor-Gene) was used to heat the scFvs in a temperature gradient while simultaneously measuring the fluorescence. The samples contained 0.5 mg/ml of scFv and 20×SYPRO® Orange (Sigma-Aldrich, cat. no. S5692, 5000×) in PBS pH 7.2. The temperature gradient was set from 30° C. to 95° C. (raising in 1° C. steps, holding time of 5 seconds per step). The fluorescence was excited at 470 nm, the emission detected at 555 nm. The midpoint melting temperatures (Tm) were calculated using Rotor-Gene 6000 Series Software 1.7. Tm of the 5 scFvs are summarized in table 2.

TABLE 2

|  | Tm |
| --- | --- |
| DLX2260 | 79° C. |
| DLX2289 | 69° C. |
| DLX2332 | 73° C. |
| DLX2296 | 71° C. |
| DLX2295 | 70° C. |

Example 6—Cross-Reactivity of DLX2295

Cross-reactivity of DLX2295 to IL-1 beta homologs from other species than human beings was assessed in ELISA. Binding to the recombinantly expressed IL-1 beta proteins of the following species was investigated: cynomolgus (Sino Biological Inc., USA, cat. no. 90010-CNAE), rhesus macaque (R&D Systems, USA, cat. no. 1318-RL/CF) and mouse IL-1 beta (BioLegend, cat. no. 575102). Binding of DLX2295 was compared to ELISA-positive control antibodies (R&D Systems, USA, goat anti-human IL-1 beta polyclonal IgG, cat. no. AB-201-NA; BioLegend, Inc., USA, biotin anti-mouse/rat IL-1 beta antibody, cat. no. 503505). Briefly, proteins were coated at a concentration of 2 mcg/ml over night at 4° C. on Maxisorp 96-well microplates in PBS pH 7.2. After blocking with 5% non-fat dry milk, increasing concentrations (0.1 mcg/ml, 0.3 mcg/ml and 1.0 mcg/ml) of DLX2295 were added to the wells. Successful coating of every protein was separately confirmed exploiting the IL-1 beta-specific control antibodies. Whereas DLX2295 was detected by Protein L-HRP (Sigma-Aldrich, USA, cat. no. P3226), the control antibodies were detected by either rabbit anti-goat IgG-HRP (Southern Biotech, cat. no. 6160-05) or by Streptavidin-HRP (BD Pharmingen, USA, cat. no. 554060). The ELISAs were developed with BM Blue POD substrate (Roche Applied Science) and the absorbance was measured at 450 nm.

DLX2295 recognized equally well human, cymonolgus and rhesus macaque IL-1 beta, while the recognition of mouse IL-1 beta was weaker.

SEQUENCE LISTING

The sequences disclosed herein are:

VL CDR1
SEQ ID No: 1
RASQDISNYLS

VL CDR2
SEQ ID No: 2
YTSKLHS

VL CDR3
SEQ ID No: 3
LQGKMLPWT

VH CDR1
SEQ ID No: 4
FSLSTSGMGVG

VH CDR2
SEQ ID No: 5
HIWWDGDESYNPSLKS

VH CDR3
SEQ ID No: 6
NRYDPPWFVD

VL of DLX2260 and DLX2289
SEQ ID No: 7
EIVMTQSPSTLSASVGDRVIITCRASQDISNYLSWYQQKPGKAPKLLIY
YTSKLHSGVPSRFSGSGSGAEFTLTISSLQPDDFATYYCLQGKMLPWTF
GQGTKLTVLG VL of DLX2295 and DLX2296
SEQ ID No: 8
DIQMTQSPSTLSASVGDRVTITCRASQDISNYLSWYQQKPGKAPKLLIY
YTSKLHSGVPSRFSGSGSGAEFTLTISSLQPEDFATYFCLQGKMLPWTF
GQGTKLEIKR VH of DLX2289
SEQ ID No: 9
EVQLVESGGGLVQPGGSLRLSCAASGFSLSTSGMGVGWVRQAPGKGLEW
VSHIWWDGDESYNPSLKSRFTISRDNSKNTLYLQMNSLRAEDTAVYYCA
KNRYDPPWFVDWGQGTLVTVSS VH of DLX2260
SEQ ID No: 10
EVQLVESGGGLVQPGGSLRLSCTASGFSLSTSGMGVGWVRQAPGKGLEW
VGHIWWDGDESYNPSLKSRFTISRDTSKNTVYLQMNSLRAEDTAVYYCA
RNRYDPPWFVDWGQGTLVTVSS VH of DLX2296
SEQ ID No: 11
EVQLVESGGGLVQPGGSLRLSCAFSGFSLSTSGMGVGWIRQAPGKGLEW
VSHIWWDGDESYNPSLKGRFTISKDTSRNTVYLQMNSLRAEDTAVYFCA
RNRYDPPWFVDWGQGTLVTVSS VH of DLX2295
SEQ D No: 12
EVQLVESGGGSVQPGGSLRLSCAFSGFSLSTSGMGVGWIRQAPGKGLEW
VSHIWWDGDESYNPSLKGRFTISKDTSRNTVYLQMNSLRAEDTASYFCA
RNRYDPPWFVDWGQGTTVTVSS VH of DLX2332
SEQ ID No: 13
EVQLVESGGGSVQPGGSLRLSCAASGFSLSTSGMGVGWVRQAPGKGLEW
VGHIWWDGDESYNPSLKSRFTISRDTSKNTVYLQMNSLRAEDTASYFCA
RNRYDPPWFVDWGQGTTVTVSS linker
SEQ ID No: 14
GGGGSGGGGSGGGGSGGGGS nucleic acid sequence of DLX2295
SEQ ID No: 15
GACATTCAGATGACGCAGTCTCCGTCTACCCTGTCCGCAAGTGTGGGTG
ATCGCGTGACAATCACCTGTCGTGCCTCACAGGACATTTCCAACTACCT
GTCCTGGTATCAACAGAAACCGGGGAAAGCACCGAAACTCTTGATCTAC
TATACGAGCAAACTGCATAGTGGAGTACCTAGCCGCTTTTCAGGCTCTG
GCAGTGGTGCGGAATTTACGCTGACCATTTCAAGCCTGCAACCCGAAGA
TTTCGCGACTTACTTCTGCTTACAGGGGAAGATGCTTCCGTGGACCTTT
GGCCAGGGGACTAAACTGGAGATCAAGGTGGAGGTGGTGGATCCGGCGG
TGGTGGCAGCGGCGGCGGTGGTTCGGGCGGCGGTGGCAGCGAAGTCCAG
CTGGTCGAATCAGGCGGTGGTTCGGTTCAACCAGGCGGCTCTTTACGCC
TCTCGTGTGCCTTTTCCGGGTTCAGTCTGAGCACGTCGGGAATGGGTGT
TGGGTGGATTCGCCAAGCTCCGGGTAAAGGCTTGGAATGGGTGAGCCAC
ATTTGGTGGGATGGAGATGAGAGCTATAACCCGTCCCTTAAAGGGCGGT
TTACCATCTCGAAAGACACCAGCCGCAATACCGTGTATCTGCAGATGAA
CAGTCTGCGTGCTGAAGATACAGCCTCGTACTTTTGCGCGCGTAATCGC
TATGATCCGCCTTGGTTCGTAGACTGGGGTCAAGGCACTACGGTCACCG
TTAGCTCT DLX2289
SEQ ID No: 16
EIVMTQSPSTLSASVGDRVIITCRASQDISNYLSWYQQKPGKAPKLLIY
YTSKLHSGVPSRFSGSGSGAEFILTISSLQPDDFATYYCLQGKMLPWTF
GQGTKLTVLGGGGGSGGGGSGGGGSGGGGSEVQLVESGGGLVQPGGSLR
LSCIAASGFSLSTSGMGVGWVRQAPGKGLEWVSHIWWDGDESYNPSLKS
RFTISRDNSKNTLYLQMNSLRAEDTAVYYCAKNRYDPPWFVDWGQGTLV
TVSS DLX2260
SEQ ID No: 17
EIVMTQSPSTLSASVGDRVIITCRASQDISNYLSWYQQKPGKAPKLLIY
YTSKLHSGVPSRFSGSGSGAEFTLTISSLUDDFATYYCLQGKMLPWTFG
QGTKLTVLGGGGGSGGGGSGGGGSGGGGSEVQLVESGGGLVQPGGSLRL
SCTASGFSLSTSGMGVGWVRQAPGKGLEWVGHIWWDGDESYNPSLKSRF
TISRDTSKNTVYLQMNSLRAEDTAVYYCARNRYDPPWFVDWGQGTLVTV
SS DLX2296
SEQ ID NO: 18
DIQMTQSPSTLSASVGDRVTITCRASQDISNYLSWYQQKPGKAPKLLIY
YTSKLHSGVPSRFSGSGSGAEFTLTISSLQPEDFATYFCLQGKMLPWTF
GQGTKLEIKRGGGGSGGGGSGGGGSGGGGSEVQLVESGGGLVQPGGSLR
LSCAFSGFSLSTSGMGVGWIRQAPGKGLEWVSHIWWDGDESYNPSLKGR
FTISKDTSRNTVYLQMNSLRAEDTAVYFCARNRYDPPWFVDWGQGTLVT
VSS

DLX2295

SEQ ID No: 19

DIQMTQSPSTLSASVGDRVTITCRASQDISNYLSWYQQKPGKAPKLLIY

YTSKLHSGVPSRFSGSGSGAEFTLTISSLQPEDFATYFCLQGKMLPWTF

GQGTKLEIKRGGGGSGGGGSGGGGSGGGGSEVQLVESGGGSVQPGGSLR

LSCAFSGFSLSTSGMGVGWIRQAPGKGLEWVSHIWWDGDESYNPSLKGR

FTISKDTSRNTVYLQMNSLRAEDTASYFCARNRYDPPWFVDWGQGTTVT

VSS

DLX2332

SEQ ID No: 20

EIVMTQSPSTLSASVGDRVIITCRASQDISNYLSWYQQKPGKAPKLLIY

YTSKLHSGVPSRFSGSGSGAEFTLTISSLQPEDFATYFCLQGKVILPWI

FGQGTKLTVLGGGGSGGGGSGGGGSGGGGSEVQLVESGGGSVQPGGSL

RLSCAASGFSLSTSGMGVGWVRQAPGKGLEWVGHIWWDGDESYNPSLKS

RFTISRDTSKNTVYLQMNSLRAEDTASYFCARNRYDPPWFVDWGQGTTV

TVSS

VH CDR2 of DLX2295

SEQ ID No: 21

HIWWDGDESYNPSLKG humanized antibody VL

SEQ ID No: 22

DIMITQSTSSLSASVGDRVTITCRASQDISNYLSWYQQKPGKAVKLLIYY
TSKLHSGVPSRFSGSGSGTDYTLTISSLQQEDFATYFCLQGKMLPWTFGQ
GTKLEIK humanized antibody VH SEQ ID No: 23

QVQLQESGPGLVKPSQTLSLTCSFSGFSLSTSGMGVGWIRQPSGKGLEWL
AHIWWDGDESYNPSLKSRLTISKDTSKNQVSLKITSVTAADTAVYFCARN
RYDPPWFVDWGQGTLVTVSS

VL DLX2332

SEQ ID No: 24

EIVMTQSPSTLSASVGDRVIITCRASQDISNYLSWYQQKPGKAPKLLIYY
TSKLHSGVPSRFSGSGSGAEFTLTISSLQPEDFATYFCLQGKIVILPWIT
GQGTKLTVLG

While there are shown and described presently preferred embodiments of the invention, it is to be understood that the invention is not limited thereto but may be otherwise variously embodied and practiced within the scope of the following claims. Since numerous modifications and alternative embodiments of the present invention will be readily apparent to those skilled in the art, this description is to be construed as illustrative only and is for the purpose of teaching those skilled in the art the best mode for carrying out the present invention. Accordingly, all suitable modifications and equivalents may be considered to fall within the scope of the following claims.

The invention claimed is:

1. A humanized antibody against IL-1 beta comprising CDR-H1, CDR-H2 and CDR-H3 amino acid sequences of SEQ ID NOs: 4, 21, and 6, respectively, and wherein
   a) position 24 of the heavy chain is an alanine residue (A);
   b) position 25 of the heavy chain is a phenylalanine residue (F);
   c) position 44 of the heavy chain is an isoleucine residue (I);
   d) position 56 of the heavy chain is a serine residue (S);
   e) position 82 of the heavy chain is a lysine residue (K);
   f) position 86 of the heavy chain is an arginine residue (R); and/or
   g) position 105 of the heavy chain is a phenylalanine residue (F); according to AHo numbering;
   and comprising CDR-L1, CDR-L2 and CDR-L3 amino acid sequences of SEQ ID NOs: 1, 2 and 3, respectively, and wherein
   h) position 1 of the light chain is an aspartic acid residue (D);
   i) position 3 of the light chain is a glu1amine residue (Q);
   j) position 20 of the light chain is a threonine residue (T);
   k) position 99 of the light chain is a glutamic acid residue (E);
   l) position 105 of the light chain is a phenylalanine residue (F);
   m) position 146 of the light chain is a glutamic residue (E);
   n) position 147 of the light chain is an isoleucine residue (I);
   o) position 148 of the light chain is a lysine residue (K); and/or
   p) position 149 of the light chain is an arginine residue (R), according to AHo numbering.

2. The antibody of claim 1, wherein the heavy chain variable domain further comprises at least one of the following residues:
   (i) Serine (S) at heavy chain amino acid position 12 (according to AHo numbering);
   (ii) Serine (S) or Threonine (T) at heavy chain amino acid position 103 (according to AHo numbering); and/or
   (iii) Serine (S) or Threonine (T) at heavy chain amino acid position 144 (according to AHo numbering).

3. The antibody of claim 1, wherein the antibody is an antibody fragment.

4. The antibody of claim 3, wherein the antibody fragment is a scFv fragment.

5. The antibody of claim 4, further comprising the linker sequence set forth in SEQ ID NO: 14.

6. The antibody of claim 1, wherein the antibody is a full-length immunoglobulin.

7. The antibody of claim 1, having an $IC_{50}$ for human IL-1 beta of lower than 10 nM, wherein the $IC_{50}$ is determined by inhibiting the IL-1 beta induced release of IL-6 from human fibroblasts.

8. The antibody of claim 7, wherein the $IC_{50}$ for human IL-1 beta is about 5 pM.

9. The antibody of claim 1, wherein the antibody is monovalent.

10. The antibody of claim 1, wherein the antibody is multivalent.

11. The antibody of claim 1, wherein the antibody has a chemical or biological modification.

12. The antibody of claim 11, wherein the antibody has a chemical or biological modification selected from the group consisting of selected from the group consisting of glycosylation, PEGylation, HESylation, albumin fusion, PASylation, labelling with a dye and/or radioisotope, conjugation with an enzyme and/or toxin, phosphorylation, hydroxylation, sulfation, and a combination thereof.

13. The antibody of claim 12, wherein the antibody has a chemical or biological modification selected from the group consisting of glycosylation, PEGylation, and HESylation.

14. A pharmaceutical composition comprising the antibody of claim 1 and pharmaceutically acceptable carrier, diluent or excipient.

15. A humanized antibody against IL-1 beta comprising a light chain variable domain comprising the amino acid sequence of SEQ ID NO: 8; and a heavy chain variable domain comprising the amino acid sequence of SEQ ID NO: 12.

16. The antibody of claim 15, further comprising the linker sequence set forth in SEQ ID NO: 14.

17. The antibody of claim 15, wherein the antibody is an antibody fragment.

18. The antibody of claim 17, wherein the antibody fragment is selected from the group consisting of a Fab, a Fab', a F(ab)'2, a scFv, and a Fv fragment.

19. The antibody of claim 18, wherein the antibody fragment is a scFv fragment.

20. The antibody of claim 19, further comprising the linker sequence set forth in SEQ ID NO: 14.

21. The antibody of claim 15, wherein the antibody is a full-length immunoglobulin.

22. The antibody of claim 15, having an $IC_{50}$ for human IL-1 beta of lower than 10 nM, wherein the $IC_{50}$ is determined by inhibiting the IL-1 beta induced release of IL-6 from human fibroblasts.

23. The antibody of claim 22, wherein the $IC_{50}$ for human IL-1 beta is about 5 pM.

24. The antibody of claim 15, wherein the antibody is monovalent or multivalent.

25. The antibody of claim 15, wherein the antibody is multivalent.

26. The antibody of claim 15, wherein the antibody has a chemical or biological modification.

27. The antibody of claim 26, wherein the chemical or biological modification is selected from the group consisting of glycosylation, PEGylation, HESylation, albumin fusion, PASylation, labelling with a dye and/or radioisotope, conjugation with an enzyme and/or toxin, phosphorylation, hydroxylation, sulfation, and a combination thereof.

28. The antibody of claim 27, wherein the antibody has a chemical or biological modification selected from the group consisting of glycosylation, PEGylation, and HESylation.

29. A composition comprising the antibody of claim 15, and further comprising a suitable carrier, diluent or excipient.

30. The composition of claim 29, wherein the composition is a cosmetic, a diagnostic or a pharmaceutical composition.

31. The composition of claim 30, wherein the composition is a pharmaceutical composition and the carrier is a pharmaceutically acceptable carrier, diluent or excipient.

32. The composition of claim 31, wherein the composition is in a form suitable for parenteral, oral, rectal, urogenital, topical, intravitreal, intraocular, otic, intranasal, dermal, sublingual, or buccal administration.

33. A kit comprising the antibody of claim 15, assay reagents, and instructions.

34. A humanized antibody against IL-1 beta, having the sequence of SEQ ID NO: 19.

* * * * *

UNITED STATES PATENT AND TRADEMARK OFFICE
CERTIFICATE OF CORRECTION

PATENT NO. : 9,914,772 B2
APPLICATION NO. : 14/740434
DATED : March 13, 2018
INVENTOR(S) : Annemarie Honegger et al.

It is certified that error appears in the above-identified patent and that said Letters Patent is hereby corrected as shown below:

In the Claims

Column 48, Claim 12, Line 29: after "consisting of" delete "selected from the group consisting of".

Signed and Sealed this
Fourth Day of December, 2018

Andrei Iancu
*Director of the United States Patent and Trademark Office*

SEQUENCE LISTING

```
<160> NUMBER OF SEQ ID NOS: 24

<210> SEQ ID NO 1
<211> LENGTH: 11
<212> TYPE: PRT
<213> ORGANISM: Mus musculus

<400> SEQUENCE: 1

Arg Ala Ser Gln Asp Ile Ser Asn Tyr Leu Ser
1               5                   10

<210> SEQ ID NO 2
<211> LENGTH: 7
<212> TYPE: PRT
<213> ORGANISM: Mus musculus

<400> SEQUENCE: 2

Tyr Thr Ser Lys Leu His Ser
1               5

<210> SEQ ID NO 3
<211> LENGTH: 9
<212> TYPE: PRT
<213> ORGANISM: Mus musculus

<400> SEQUENCE: 3

Leu Gln Gly Lys Met Leu Pro Trp Thr
1               5
```

```
<210> SEQ ID NO 4
<211> LENGTH: 11
<212> TYPE: PRT
<213> ORGANISM: Mus musculus

<400> SEQUENCE: 4

Phe Ser Leu Ser Thr Ser Gly Met Gly Val Gly
1               5                   10

<210> SEQ ID NO 5
<211> LENGTH: 16
<212> TYPE: PRT
<213> ORGANISM: Artificial Sequence
<220> FEATURE:
<223> OTHER INFORMATION: VH CDR2

<400> SEQUENCE: 5

His Ile Trp Trp Asp Gly Asp Glu Ser Tyr Asn Pro Ser Leu Lys Ser
1               5                   10                  15

<210> SEQ ID NO 6
<211> LENGTH: 10
<212> TYPE: PRT
<213> ORGANISM: Mus musculus

<400> SEQUENCE: 6

Asn Arg Tyr Asp Pro Pro Trp Phe Val Asp
1               5                   10

<210> SEQ ID NO 7
<211> LENGTH: 108
<212> TYPE: PRT
<213> ORGANISM: Artificial Sequence
<220> FEATURE:
<223> OTHER INFORMATION: VL of DLX2260 and DLX2289

<400> SEQUENCE: 7

Glu Ile Val Met Thr Gln Ser Pro Ser Thr Leu Ser Ala Ser Val Gly
1               5                   10                  15

Asp Arg Val Ile Ile Thr Cys Arg Ala Ser Gln Asp Ile Ser Asn Tyr
            20                  25                  30

Leu Ser Trp Tyr Gln Gln Lys Pro Gly Lys Ala Pro Lys Leu Leu Ile
        35                  40                  45

Tyr Tyr Thr Ser Lys Leu His Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Leu Gln Gly Lys Met Leu Pro Trp
                85                  90                  95

Thr Phe Gly Gln Gly Thr Lys Leu Thr Val Leu Gly
            100                 105

<210> SEQ ID NO 8
<211> LENGTH: 108
<212> TYPE: PRT
<213> ORGANISM: Artificial Sequence
<220> FEATURE:
<223> OTHER INFORMATION: VL of DLX2295 and DLX2296

<400> SEQUENCE: 8

Asp Ile Gln Met Thr Gln Ser Pro Ser Thr Leu Ser Ala Ser Val Gly
1               5                   10                  15
```

```
Asp Arg Val Thr Ile Thr Cys Arg Ala Ser Gln Asp Ile Ser Asn Tyr
            20                  25                  30

Leu Ser Trp Tyr Gln Gln Lys Pro Gly Lys Ala Pro Lys Leu Leu Ile
        35                  40                  45

Tyr Tyr Thr Ser Lys Leu His Ser Gly Val Pro Ser Arg Phe Ser Gly
50                  55                  60

Ser Gly Ser Gly Ala Glu Phe Thr Leu Thr Ile Ser Ser Leu Gln Pro
65                  70                  75                  80

Glu Asp Phe Ala Thr Tyr Phe Cys Leu Gln Gly Lys Met Leu Pro Trp
                85                  90                  95

Thr Phe Gly Gln Gly Thr Lys Leu Glu Ile Lys Arg
            100                 105
```

<210> SEQ ID NO 9
<211> LENGTH: 120
<212> TYPE: PRT
<213> ORGANISM: Artificial Sequence
<220> FEATURE:
<223> OTHER INFORMATION: VH of DLX2289

<400> SEQUENCE: 9

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Ser
            20                  25                  30

Gly Met Gly Val Gly Trp Val Arg Gln Ala Pro Gly Lys Gly Leu Glu
        35                  40                  45

Trp Val Ser His Ile Trp Trp Asp Gly Asp Glu Ser Tyr Asn Pro Ser
50                  55                  60

Leu Lys Ser Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Asn Arg Tyr Asp Pro Pro Trp Phe Val Asp Trp Gly Gln
            100                 105                 110

Gly Thr Leu Val Thr Val Ser Ser
        115                 120
```

<210> SEQ ID NO 10
<211> LENGTH: 120
<212> TYPE: PRT
<213> ORGANISM: Artificial Sequence
<220> FEATURE:
<223> OTHER INFORMATION: VH of DLX2260

<400> SEQUENCE: 10

```
Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Thr Ser
            20                  25                  30

Gly Met Gly Val Gly Trp Val Arg Gln Ala Pro Gly Lys Gly Leu Glu
        35                  40                  45

Trp Val Gly His Ile Trp Trp Asp Gly Asp Glu Ser Tyr Asn Pro Ser
50                  55                  60

Leu Lys Ser Arg Phe Thr Ile Ser Arg Asp Thr Ser Lys Asn Thr Val
65                  70                  75                  80
```

```
Tyr Leu Gln Met Asn Ser Leu Arg Ala Glu Asp Thr Ala Val Tyr Tyr
                85                  90                  95

Cys Ala Arg Asn Arg Tyr Asp Pro Pro Trp Phe Val Asp Trp Gly Gln
            100                 105                 110

Gly Thr Leu Val Thr Val Ser Ser
        115                 120

<210> SEQ ID NO 11
<211> LENGTH: 120
<212> TYPE: PRT
<213> ORGANISM: Artificial Sequence
<220> FEATURE:
<223> OTHER INFORMATION: VH of DLX2296

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Phe Ser Gly Phe Ser Leu Ser Thr Ser
            20                  25                  30

Gly Met Gly Val Gly Trp Ile Arg Gln Ala Pro Gly Lys Gly Leu Glu
        35                  40                  45

Trp Val Ser His Ile Trp Trp Asp Gly Asp Glu Ser Tyr Asn Pro Ser
    50                  55                  60

Leu Lys Gly Arg Phe Thr Ile Ser Lys Asp Thr Ser Arg Asn Thr Val
65                  70                  75                  80

Tyr Leu Gln Met Asn Ser Leu Arg Ala Glu Asp Thr Ala Val Tyr Phe
                85                  90                  95

Cys Ala Arg Asn Arg Tyr Asp Pro Pro Trp Phe Val Asp Trp Gly Gln
            100                 105                 110

Gly Thr Leu Val Thr Val Ser Ser
        115                 120

<210> SEQ ID NO 12
<211> LENGTH: 120
<212> TYPE: PRT
<213> ORGANISM: Artificial Sequence
<220> FEATURE:
<223> OTHER INFORMATION: VH of DLX2295

<400> SEQUENCE: 12

Glu Val Gln Leu Val Glu Ser Gly Gly Gly Ser Val Gln Pro Gly Gly
1               5                   10                  15

Ser Leu Arg Leu Ser Cys Ala Phe Ser Gly Phe Ser Leu Ser Thr Ser
            20                  25                  30

Gly Met Gly Val Gly Trp Ile Arg Gln Ala Pro Gly Lys Gly Leu Glu
        35                  40                  45

Trp Val Ser His Ile Trp Trp Asp Gly Asp Glu Ser Tyr Asn Pro Ser
    50                  55                  60

Leu Lys Gly Arg Phe Thr Ile Ser Lys Asp Thr Ser Arg Asn Thr Val
65                  70                  75                  80

Tyr Leu Gln Met Asn Ser Leu Arg Ala Glu Asp Thr Ala Ser Tyr Phe
                85                  90                  95

Cys Ala Arg Asn Arg Tyr Asp Pro Pro Trp Phe Val Asp Trp Gly Gln
            100                 105                 110

Gly Thr Thr Val Thr Val Ser Ser
        115                 120
```

<210> SEQ ID NO 13
<211> LENGTH: 120
<212> TYPE: PRT
<213> ORGANISM: Artificial Sequence
<220> FEATURE:
<223> OTHER INFORMATION: VH of DLX2332

<400> SEQUENCE: 13

Glu Val Gln Leu Val Glu Ser Gly Gly Gly Ser Val Gln Pro Gly Gly
1               5                   10                  15

Ser Leu Arg Leu Ser Cys Ala Ala Ser Gly Phe Ser Leu Ser Thr Ser
            20                  25                  30

Gly Met Gly Val Gly Trp Val Arg Gln Ala Pro Gly Lys Gly Leu Glu
        35                  40                  45

Trp Val Gly His Ile Trp Trp Asp Gly Asp Ser Tyr Asn Pro Ser
    50                  55                  60

Leu Lys Ser Arg Phe Thr Ile Ser Arg Asp Thr Ser Lys Asn Thr Val
65                  70                  75                  80

Tyr Leu Gln Met Asn Ser Leu Arg Ala Glu Asp Thr Ala Ser Tyr Phe
                85                  90                  95

Cys Ala Arg Asn Arg Tyr Asp Pro Pro Trp Phe Val Asp Trp Gly Gln
            100                 105                 110

Gly Thr Thr Val Thr Val Ser Ser
        115                 120

<210> SEQ ID NO 14
<211> LENGTH: 20
<212> TYPE: PRT
<213> ORGANISM: Artificial Sequence
<220> FEATURE:
<223> OTHER INFORMATION: linker

<400> SEQUENCE: 14

Gly Gly Gly Gly Ser Gly Gly Gly Ser Gly Gly Gly Ser Gly
1               5                   10                  15

Gly Gly Gly Ser
            20

<210> SEQ ID NO 15
<211> LENGTH: 744
<212> TYPE: DNA
<213> ORGANISM: Artificial Sequence
<220> FEATURE:
<223> OTHER INFORMATION: DNA sequence of DLX2295

<400> SEQUENCE: 15
gacattcaga tgacgcagtc tccgtctacc ctgtccgcaa gtgtgggtga tcgcgtgaca      60
atcacctgtc gtgcctcaca ggacatttcc aactacctgt cctggtatca acagaaaccg     120
gggaaagcac cgaaactctt gatctactat acgagcaaac tgcatagtgg agtacctagc     180
cgcttttcag gctctggcag tggtgcggaa tttacgctga ccatttcaag cctgcaaccc     240
gaagatttcg cgacttactt ctgcttacag gggaagatgc ttccgtggac ctttggccag     300
gggactaaac tggagatcaa gcgtggaggt ggtggatccg gcggtggtgg cagcggcggc     360
ggtggttcgg gcggcggtgg cagcgaagtc cagctggtcg aatcaggcgg tggttcggtt     420
caaccaggcg gctctttacg cctctcgtgt gcctttccg ggttcagtct gagcacgtcg      480
ggaatgggtg ttgggtggat cgccaagct ccgggtaaag gcttggaatg ggtgagccac      540

```
atttggtggg atggagatga gagctataac ccgtccctta aagggcggtt taccatctcg    600
aaagacacca gccgcaatac cgtgtatctg cagatgaaca gtctgcgtgc tgaagataca    660
gcctcgtact tttgcgcgcg taatcgctat gatccgcctt ggttcgtaga ctggggtcaa    720
ggcactacgg tcaccgttag ctct                                           744
```

<210> SEQ ID NO 16
<211> LENGTH: 248
<212> TYPE: PRT
<213> ORGANISM: Artificial Sequence
<220> FEATURE:
<223> OTHER INFORMATION: DLX2289

<400> SEQUENCE: 16

```
Glu Ile Val Met Thr Gln Ser Pro Ser Thr Leu Ser Ala Ser Val Gly
1               5                   10                  15

Asp Arg Val Ile Ile Thr Cys Arg Ala Ser Gln Asp Ile Ser Asn Tyr
                20                  25                  30

Leu Ser Trp Tyr Gln Gln Lys Pro Gly Lys Ala Pro Lys Leu Leu Ile
            35                  40                  45

Tyr Tyr Thr Ser Lys Leu His Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Leu Gln Gly Lys Met Leu Pro Trp
                85                  90                  95

Thr Phe Gly Gln Gly Thr Lys Leu Thr Val Leu Gly Gly Gly Gly Gly
                100                 105                 110

Ser Gly Gly Gly Gly Ser Gly Gly Gly Ser Gly Gly Gly Gly Ser
            115                 120                 125

Glu Val Gln Leu Val Glu Ser Gly Gly Gly Leu Val Gln Pro Gly Gly
    130                 135                 140

Ser Leu Arg Leu Ser Cys Ala Ala Ser Gly Phe Ser Leu Ser Thr Ser
145                 150                 155                 160

Gly Met Gly Val Gly Trp Val Arg Gln Ala Pro Gly Lys Gly Leu Glu
                165                 170                 175

Trp Val Ser His Ile Trp Trp Asp Gly Asp Glu Ser Tyr Asn Pro Ser
                180                 185                 190

Leu Lys Ser Arg Phe Thr Ile Ser Arg Asp Asn Ser Lys Asn Thr Leu
            195                 200                 205

Tyr Leu Gln Met Asn Ser Leu Arg Ala Glu Asp Thr Ala Val Tyr Tyr
    210                 215                 220

Cys Ala Lys Asn Arg Tyr Asp Pro Pro Trp Phe Val Asp Trp Gly Gln
225                 230                 235                 240

Gly Thr Leu Val Thr Val Ser Ser
                245
```

<210> SEQ ID NO 17
<211> LENGTH: 248
<212> TYPE: PRT
<213> ORGANISM: Artificial Sequence
<220> FEATURE:
<223> OTHER INFORMATION: DLX2260

<400> SEQUENCE: 17

```
Glu Ile Val Met Thr Gln Ser Pro Ser Thr Leu Ser Ala Ser Val Gly
1               5                   10                  15
```

```
Asp Arg Val Ile Ile Thr Cys Arg Ala Ser Gln Asp Ile Ser Asn Tyr
            20                  25                  30

Leu Ser Trp Tyr Gln Gln Lys Pro Gly Lys Ala Pro Lys Leu Leu Ile
        35                  40                  45

Tyr Tyr Thr Ser Lys Leu His Ser Gly Val Pro Ser Arg Phe Ser Gly
 50                  55                  60

Ser Gly Ser Gly Ala Glu Phe Thr Leu Thr Ile Ser Ser Leu Gln Pro
 65                  70                  75                  80

Asp Asp Phe Ala Thr Tyr Tyr Cys Leu Gln Gly Lys Met Leu Pro Trp
                85                  90                  95

Thr Phe Gly Gln Gly Thr Lys Leu Thr Val Leu Gly Gly Gly Gly Gly
            100                 105                 110

Ser Gly Gly Gly Gly Ser Gly Gly Gly Ser Gly Gly Gly Gly Ser
            115                 120                 125

Glu Val Gln Leu Val Glu Ser Gly Gly Leu Val Gln Pro Gly Gly
            130                 135                 140

Ser Leu Arg Leu Ser Cys Thr Ala Ser Gly Phe Ser Leu Ser Thr Ser
145                 150                 155                 160

Gly Met Gly Val Gly Trp Val Arg Gln Ala Pro Gly Lys Gly Leu Glu
                165                 170                 175

Trp Val Gly His Ile Trp Trp Asp Gly Asp Glu Ser Tyr Asn Pro Ser
                180                 185                 190

Leu Lys Ser Arg Phe Thr Ile Ser Arg Asp Thr Ser Lys Asn Thr Val
                195                 200                 205

Tyr Leu Gln Met Asn Ser Leu Arg Ala Glu Asp Thr Ala Val Tyr Tyr
            210                 215                 220

Cys Ala Arg Asn Arg Tyr Asp Pro Pro Trp Phe Val Asp Trp Gly Gln
225                 230                 235                 240

Gly Thr Leu Val Thr Val Ser Ser
                245

<210> SEQ ID NO 18
<211> LENGTH: 248
<212> TYPE: PRT
<213> ORGANISM: Artificial Sequence
<220> FEATURE:
<223> OTHER INFORMATION: DLX2296

<400> SEQUENCE: 18

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Asp Ile Ser Asn Tyr
            20                  25                  30

Leu Ser Trp Tyr Gln Gln Lys Pro Gly Lys Ala Pro Lys Leu Leu Ile
        35                  40                  45

Tyr Tyr Thr Ser Lys Leu His Ser Gly Val Pro Ser Arg Phe Ser Gly
 50                  55                  60

Ser Gly Ser Gly Ala Glu Phe Thr Leu Thr Ile Ser Ser Leu Gln Pro
 65                  70                  75                  80

Glu Asp Phe Ala Thr Tyr Phe Cys Leu Gln Gly Lys Met Leu Pro Trp
                85                  90                  95

Thr Phe Gly Gln Gly Thr Lys Leu Glu Ile Lys Arg Gly Gly Gly Gly
            100                 105                 110

Ser Gly Gly Gly Gly Ser Gly Gly Gly Gly Ser Gly Gly Gly Gly Ser
            115                 120                 125
```

```
Glu Val Gln Leu Val Glu Ser Gly Gly Gly Leu Val Gln Pro Gly Gly
            130                 135                 140

Ser Leu Arg Leu Ser Cys Ala Phe Ser Gly Phe Ser Leu Ser Thr Ser
145                 150                 155                 160

Gly Met Gly Val Gly Trp Ile Arg Gln Ala Pro Gly Lys Gly Leu Glu
                165                 170                 175

Trp Val Ser His Ile Trp Trp Asp Gly Asp Glu Ser Tyr Asn Pro Ser
                180                 185                 190

Leu Lys Gly Arg Phe Thr Ile Ser Lys Asp Thr Ser Arg Asn Thr Val
                195                 200                 205

Tyr Leu Gln Met Asn Ser Leu Arg Ala Glu Asp Thr Ala Val Tyr Phe
                210                 215                 220

Cys Ala Arg Asn Arg Tyr Asp Pro Pro Trp Phe Val Asp Trp Gly Gln
225                 230                 235                 240

Gly Thr Leu Val Thr Val Ser Ser
                245

<210> SEQ ID NO 19
<211> LENGTH: 248
<212> TYPE: PRT
<213> ORGANISM: Artificial Sequence
<220> FEATURE:
<223> OTHER INFORMATION: DLX2295

<400> SEQUENCE: 19

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Ser Trp Tyr Gln Gln Lys Pro Gly Lys Ala Pro Lys Leu Leu Ile
            35                  40                  45

Tyr Tyr Thr Ser Lys Leu His Ser Gly Val Pro Ser Arg Phe Ser Gly
50                  55                  60

Ser Gly Ser Gly Ala Glu Phe Thr Leu Thr Ile Ser Ser Leu Gln Pro
65                  70                  75                  80

Glu Asp Phe Ala Thr Tyr Phe Cys Leu Gln Gly Lys Met Leu Pro Trp
                85                  90                  95

Thr Phe Gly Gln Gly Thr Lys Leu Glu Ile Lys Arg Gly Gly Gly Gly
                100                 105                 110

Ser Gly Gly Gly Gly Ser Gly Gly Gly Ser Gly Gly Gly Gly Ser
            115                 120                 125

Glu Val Gln Leu Val Glu Ser Gly Gly Gly Leu Val Gln Pro Gly Gly
            130                 135                 140

Ser Leu Arg Leu Ser Cys Ala Phe Ser Gly Phe Ser Leu Ser Thr Ser
145                 150                 155                 160

Gly Met Gly Val Gly Trp Ile Arg Gln Ala Pro Gly Lys Gly Leu Glu
                165                 170                 175

Trp Val Ser His Ile Trp Trp Asp Gly Asp Glu Ser Tyr Asn Pro Ser
                180                 185                 190

Leu Lys Gly Arg Phe Thr Ile Ser Lys Asp Thr Ser Arg Asn Thr Val
                195                 200                 205

Tyr Leu Gln Met Asn Ser Leu Arg Ala Glu Asp Thr Ala Ser Tyr Phe
                210                 215                 220

Cys Ala Arg Asn Arg Tyr Asp Pro Pro Trp Phe Val Asp Trp Gly Gln
225                 230                 235                 240
```

Gly Thr Thr Val Thr Val Ser Ser
            245

<210> SEQ ID NO 20
<211> LENGTH: 248
<212> TYPE: PRT
<213> ORGANISM: Artificial Sequence
<220> FEATURE:
<223> OTHER INFORMATION: DLX2332

<400> SEQUENCE: 20

Glu Ile Val Met Thr Gln Ser Pro Ser Thr Leu Ser Ala Ser Val Gly
1               5                   10                  15

Asp Arg Val Ile Ile Thr Cys Arg Ala Ser Gln Asp Ile Ser Asn Tyr
            20                  25                  30

Leu Ser Trp Tyr Gln Gln Lys Pro Gly Lys Ala Pro Lys Leu Leu Ile
        35                  40                  45

Tyr Tyr Thr Ser Lys Leu His Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Glu Asp Phe Ala Thr Tyr Phe Cys Leu Gln Gly Lys Met Leu Pro Trp
                85                  90                  95

Thr Phe Gly Gln Gly Thr Lys Leu Thr Val Leu Gly Gly Gly Gly
            100                 105                 110

Ser Gly Gly Gly Gly Ser Gly Gly Gly Ser Gly Gly Gly Gly Ser
        115                 120                 125

Glu Val Gln Leu Val Glu Ser Gly Gly Ser Val Gln Pro Gly Gly
    130                 135                 140

Ser Leu Arg Leu Ser Cys Ala Ala Ser Gly Phe Ser Leu Ser Thr Ser
145                 150                 155                 160

Gly Met Gly Val Gly Trp Val Arg Gln Ala Pro Gly Lys Gly Leu Glu
                165                 170                 175

Trp Val Gly His Ile Trp Trp Asp Gly Asp Glu Ser Tyr Asn Pro Ser
            180                 185                 190

Leu Lys Ser Arg Phe Thr Ile Ser Arg Asp Thr Ser Lys Asn Thr Val
        195                 200                 205

Tyr Leu Gln Met Asn Ser Leu Arg Ala Glu Asp Thr Ala Ser Tyr Phe
    210                 215                 220

Cys Ala Arg Asn Arg Tyr Asp Pro Pro Trp Phe Val Asp Trp Gly Gln
225                 230                 235                 240

Gly Thr Thr Val Thr Val Ser Ser
            245

<210> SEQ ID NO 21
<211> LENGTH: 16
<212> TYPE: PRT
<213> ORGANISM: Artificial Sequence
<220> FEATURE:
<223> OTHER INFORMATION: CDR2 of DLX2295

<400> SEQUENCE: 21

His Ile Trp Trp Asp Gly Asp Glu Ser Tyr Asn Pro Ser Leu Lys Gly
1               5                   10                  15

<210> SEQ ID NO 22
<211> LENGTH: 107
<212> TYPE: PRT

```
<213> ORGANISM: Artificial Sequence
<220> FEATURE:
<223> OTHER INFORMATION: humanized antibody VL

<400> SEQUENCE: 22

Asp Ile Gln Met Thr Gln Ser Thr Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ser Trp Tyr Gln Gln Lys Pro Gly Lys Ala Val Lys Leu Leu Ile
        35                  40                  45

Tyr Tyr Thr Ser Lys Leu His Ser Gly Val Pro Ser Arg Phe Ser Gly
50                  55                  60

Ser Gly Ser Gly Thr Asp Tyr Thr Leu Thr Ile Ser Ser Leu Gln Gln
65                  70                  75                  80

Glu Asp Phe Ala Thr Tyr Phe Cys Leu Gln Gly Lys Met Leu Pro Trp
                85                  90                  95

Thr Phe Gly Gln Gly Thr Lys Leu Glu Ile Lys
            100                 105

<210> SEQ ID NO 23
<211> LENGTH: 120
<212> TYPE: PRT
<213> ORGANISM: Artificial Sequence
<220> FEATURE:
<223> OTHER INFORMATION: humanized antibody VH

<400> SEQUENCE: 23

Gln Val Gln Leu Gln Glu Ser Gly Pro Gly Leu Val Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
50                  55                  60

Leu Lys Ser Arg Leu Thr Ile Ser Lys Asp Thr Ser Lys Asn Gln Val
65                  70                  75                  80

Ser Leu Lys Ile Thr Ser Val Thr Ala Ala Asp Thr Ala Val Tyr Phe
                85                  90                  95

Cys Ala Arg Asn Arg Tyr Asp Pro Pro Trp Phe Val Asp Trp Gly Gln
            100                 105                 110

Gly Thr Leu Val Thr Val Ser Ser
        115                 120

<210> SEQ ID NO 24
<211> LENGTH: 108
<212> TYPE: PRT
<213> ORGANISM: Artificial Sequence
<220> FEATURE:
<223> OTHER INFORMATION: VL DLX2332

<400> SEQUENCE: 24

Glu Ile Val Met Thr Gln Ser Pro Ser Thr Leu Ser Ala Ser Val Gly
1               5                   10                  15

Asp Arg Val Ile Ile Thr Cys Arg Ala Ser Gln Asp Ile Ser Asn Tyr
            20                  25                  30

Leu Ser Trp Tyr Gln Gln Lys Pro Gly Lys Ala Pro Lys Leu Leu Ile
        35                  40                  45
```

```
Tyr Tyr Thr Ser Lys Leu His Ser Gly Val Pro Ser Arg Phe Ser Gly
    50              55                  60

Ser Gly Ser Gly Ala Glu Phe Thr Leu Thr Ile Ser Ser Leu Gln Pro
65              70                  75                  80

Glu Asp Phe Ala Thr Tyr Phe Cys Leu Gln Gly Lys Met Leu Pro Trp
                85              90                  95

Thr Phe Gly Gln Gly Thr Lys Leu Thr Val Leu Gly
            100             105
```